US011266821B2

(12) United States Patent
Pratt et al.

(10) Patent No.: US 11,266,821 B2
(45) Date of Patent: Mar. 8, 2022

(54) AUTONOMOUS FLUID INSTILLATION SYSTEM AND METHOD WITH TISSUE SITE PRESSURE MONITORING

(71) Applicant: KCI Licensing, Inc., San Antonio, TX (US)

(72) Inventors: Benjamin Andrew Pratt, Poole (GB); Christopher Brian Locke, Bournemouth (GB)

(73) Assignee: KCI Licensing, Inc., San Antonio, TX (US)

(*) Notice: Subject to any disclaimer, the term of this patent is extended or adjusted under 35 U.S.C. 154(b) by 694 days.

(21) Appl. No.: 15/874,749

(22) Filed: Jan. 18, 2018

(65) Prior Publication Data
US 2018/0140814 A1 May 24, 2018

Related U.S. Application Data

(63) Continuation of application No. 14/561,718, filed on Dec. 5, 2014, now Pat. No. 9,907,940.
(Continued)

(51) Int. Cl.
*A61M 37/00* (2006.01)
*A61M 39/22* (2006.01)
(Continued)

(52) U.S. Cl.
CPC ....... *A61M 37/00* (2013.01); *A61F 13/00068* (2013.01); *A61M 1/85* (2021.05);
(Continued)

(58) Field of Classification Search
CPC .. A61M 3/022; A61M 1/0084; A61M 1/0088; A61M 39/22; A61M 3/0258;
(Continued)

(56) References Cited

U.S. PATENT DOCUMENTS 1,355,846 A   10/1920   Rannells
2,547,758 A   4/1951   Keeling
(Continued)

FOREIGN PATENT DOCUMENTS

AU   550575 B2   3/1986
AU   745271 B2   3/2002
(Continued)

OTHER PUBLICATIONS

Rycerz et al. "V.A.C Ulta™ NPWT System Made Easy", Wounds International vol. 3, No. 3, Sep. 1, 2012, pp. 1-6.
(Continued)

*Primary Examiner* — Tatyana Zalukaeva
*Assistant Examiner* — Jessica R Arble

(57) ABSTRACT

A system and method for providing fluid to a tissue site is described. The method fluidly couples an instillation therapy system to the tissue site and monitors a pressure supplied to the tissue site by a reduced-pressure source with the instillation therapy system for a time period. The method provides fluid to the tissue site with the instillation therapy system in response to the pressure at the tissue site during the time period. The system includes a pressure sensor fluidly coupled to the tissue site to measure a pressure proximate the tissue site. A valve and a flow meter are fluidly between a fluid reservoir and the tissue site. A controller is communicatively coupled to the pressure sensor and the valve and configured to monitor the pressure at the tissue site and a volume of fluid flow to the tissue and, in response, operate the valve.

13 Claims, 8 Drawing Sheets

Related U.S. Application Data

(60) Provisional application No. 61/917,773, filed on Dec. 18, 2013.

(51) Int. Cl.
*A61F 13/00* (2006.01)
*A61M 3/02* (2006.01)
*A61M 1/00* (2006.01)

(52) U.S. Cl.
CPC .............. *A61M 1/90* (2021.05); *A61M 3/022* (2014.02); *A61M 39/22* (2013.01); *A61M 1/0062* (2013.01); *A61M 3/0258* (2013.01); *A61M 3/0283* (2013.01); *A61M 2037/0007* (2013.01); *A61M 2039/226* (2013.01); *A61M 2205/3334* (2013.01); *A61M 2205/3344* (2013.01)

(58) Field of Classification Search
CPC .............. A61M 3/0283; A61M 1/0062; A61M 2205/3344; A61M 2037/0007; A61M 2039/226; A61M 2205/3334; A61M 1/0058; A61F 13/00068
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2009/0299308 A1* | 12/2009 | Kazala, Jr .............. A61H 1/008 604/319 |
| 2010/0168688 A1* | 7/2010 | Santora .............. A61M 25/0032 604/313 |
| 2010/0262078 A1 | 10/2010 | Blomquist |

(56) References Cited

U.S. PATENT DOCUMENTS

| | | | | |
|---|---|---|---|---|
| 2012/0035560 | A1* | 2/2012 | Eddy | A61M 1/0088 604/313 |
| 2012/0160342 | A1* | 6/2012 | Weissenbach | B01D 61/20 137/343 |
| 2012/0302976 | A1* | 11/2012 | Locke | A61F 13/00068 604/318 |
| 2013/0035659 | A1* | 2/2013 | Hungerford | F04B 49/065 604/500 |
| 2013/0085462 | A1* | 4/2013 | Nip | A61F 13/00068 604/315 |
| 2013/0150813 | A1* | 6/2013 | Gordon | A61M 1/0052 604/318 |
| 2013/0248446 | A1 | 9/2013 | Frugier | |
| 2014/0107613 | A1 | 4/2014 | Keith et al. | |
| 2014/0163491 | A1 | 6/2014 | Schuessler et al. | |
| 2015/0080788 | A1 | 3/2015 | Blott et al. | |
| 2015/0290364 | A1* | 10/2015 | Wall | A61F 13/00068 604/24 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 0880953 A2 | 12/1998 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2012166428 A1 | 12/2012 |
| WO | 2013116158 A2 | 8/2013 |
| WO | 2013117318 A1 | 8/2013 |

OTHER PUBLICATIONS

International Search Report and Written Opinion for PCT/US2014/068892, dated Mar. 25, 2015.
Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. YU.N., et al; "Active Wound Drainage", Vestnki Khirurgi, vol. 138, Issue 4, 1987, and 7 page English translation thereof.
Davydov, YU.A., et al; "Bacteriological and Cytological Assessment of Vacuum Therapy for Purulent Wounds" Vestnik Khirugi, Oct. 1988, pp. 48-52, and 8 page English translation thereof.
Davydov, YU.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

(56) References Cited

OTHER PUBLICATIONS

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

\* cited by examiner

AUTONOMOUS FLUID INSTALLATION SYSTEM AND METHOD WITH TISSUE SITE PRESSURE MONITORING

RELATED APPLICATIONS

This application is a continuation of U.S. patent application Ser. No. 14/561,718, filed Dec. 5, 2014, which claims the benefit, under 35 USC § 119(e), of the filing of U.S. Provisional Patent Application No. 61/917,773, entitled "Autonomous Fluid Installation System and Method with Tissue Site Pressure Monitoring," filed Dec. 18, 2013, which is incorporated herein by reference for all purposes.

TECHNICAL FIELD

The present invention relates generally to tissue treatment systems and more particularly, but without limitation, to a system and method for providing instillation therapy to a tissue site.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds with reduced pressure may be commonly referred to as "reduced-pressure therapy," but is also known by other names, including "negative-pressure therapy," "negative-pressure wound therapy," "reduced-pressure wound therapy," "vacuum therapy," and "vacuum-assisted closure," for example. Reduced-pressure therapy may provide a number of benefits, including migration of epithelial and subcutaneous tissues, improved blood flow, and micro-deformation of tissue at a tissue site. Together, these benefits can increase development of granulation tissue and reduce healing times.

In addition, the delivery of therapeutic fluids (e.g. saline or antibiotic fluids) to the tissue site can also provide benefits to healing of a tissue site. Treatment of tissue sites with the delivery of therapeutic fluids may also be referred to as "instillation therapy." Instillation therapy may assist in cleaning the tissue site by aiding in the removal of infectious agents or necrotic tissue. The therapeutic fluids used in instillation therapy may also provide medicinal fluids, such as antibiotics, anti-fungals, antiseptics, analgesics, or other similar substances, to aid in the treatment of a tissue site.

While the clinical benefits of reduced-pressure therapy and instillation therapy are widely known, the cost and complexity of reduced-pressure therapy and instillation therapy can be a limiting factor in its application, and the development and operation of reduced-pressure systems, components, and processes continues to present significant challenges to manufacturers, healthcare providers, and patients.

BRIEF SUMMARY

In one example embodiment, a method for providing fluid to a tissue site may be described. An instillation therapy system may be fluidly coupled to the tissue site, and a pressure supplied to the tissue site by a reduced-pressure source may be monitored with the instillation therapy system for a time period. Fluid may be provided to the tissue site with the instillation therapy system in response to the pressure at the tissue site during the time period.

In another example embodiment, a method for providing fluid to a tissue site may be described. An instillation therapy system may be fluidly coupled to the tissue site. A reduced-pressure treatment system fluidly coupled to the tissue site may be operated to provide reduced-pressure therapy in an intermittent mode, and the instillation therapy system may monitor a pressure at the tissue site. A pressure profile of the reduced-pressure therapy at the tissue site may be determined. A valve fluidly coupled between the tissue site and a fluid reservoir may be opened in response to the pressure profile.

In still another embodiment, a system for providing instillation therapy to a tissue site may be described. The system may include a fluid interface configured to be fluidly coupled to the tissue site and a pressure sensor fluidly coupled to the fluid interface and configured to measure a pressure proximate the tissue site. The system may also include a valve fluidly coupled to the fluid interface. The valve may have an open position configured to permit fluid communication through the valve and a closed position configured to prevent fluid communication through the valve. The system may have a flow meter configured to be fluidly coupled between the valve and the fluid interface and a fluid reservoir fluidly coupled to the valve. The system may include a controller communicatively coupled to the pressure sensor and the valve. The controller may be configured to monitor the pressure measured by the pressure sensor and a volume of fluid flow through the flow meter and, in response, operate the valve.

In yet another example embodiment, a method for providing fluid to a tissue site may be described. An instillation therapy system may be fluidly coupled to the tissue site and operated in a training mode. A pressure profile of a reduced pressure source fluidly coupled to the tissue site may be determined in response to the training mode. In response to the pressure profile, the instillation therapy system may deliver fluid to the tissue site.

In yet still another example embodiment, a method for delivering fluid to a tissue site may be described. An instillation therapy system may be coupled to the tissue site, and the instillation therapy system may monitor a pressure at the tissue site. Fluids may be delivered to the tissue site if the pressure at the tissue site is about a trigger pressure, and the instillation therapy system may continue to monitor the pressure at the tissue site if the pressure at the tissue site is not about the trigger pressure. A fluid flow to the tissue site may be monitored in response to delivering fluids to the tissue site, and the instillation therapy system may determine if the fluid flow is about a dosage of fluids. If the fluid flow is about the dosage of fluids, the fluid flow may be stopped. And if the fluid flow is not about the dosage of fluids, the instillation therapy system may determine if a reduced-pressure source fluidly coupled to the tissue site is about to start an on period. If the reduced-pressure source is not about to start the on period, fluids may continue to be delivered. If the reduced-pressure source is about to enter the on period, fluid may stop being delivered, and the trigger pressure may be incremented if the reduced-pressure source is about to start the on period.

Other objects, features, and advantages of the embodiments described herein will become apparent with reference to the drawings and detailed description that follow.

DESCRIPTION OF EXAMPLE EMBODIMENTS

New and useful systems and methods for providing instillation therapy in a reduced-pressure therapy environment are set forth in the appended claims. Objectives, advantages, and a preferred mode of making and using the systems and methods may be understood best by reference to the following detailed description in conjunction with the accompanying drawings. The description provides information that enables a person skilled in the art to make and use the claimed subject matter, but may omit certain details already well-known in the art. Moreover, descriptions of various alternatives using terms such as "or" do not necessarily require mutual exclusivity unless clearly required by the context. The claimed subject matter may also encompass alternative embodiments not specifically described in detail. The following detailed description is, therefore, to be taken as illustrative and not limiting.

The example embodiments may also be described herein with reference to spatial relationships between various elements or to the spatial orientations of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
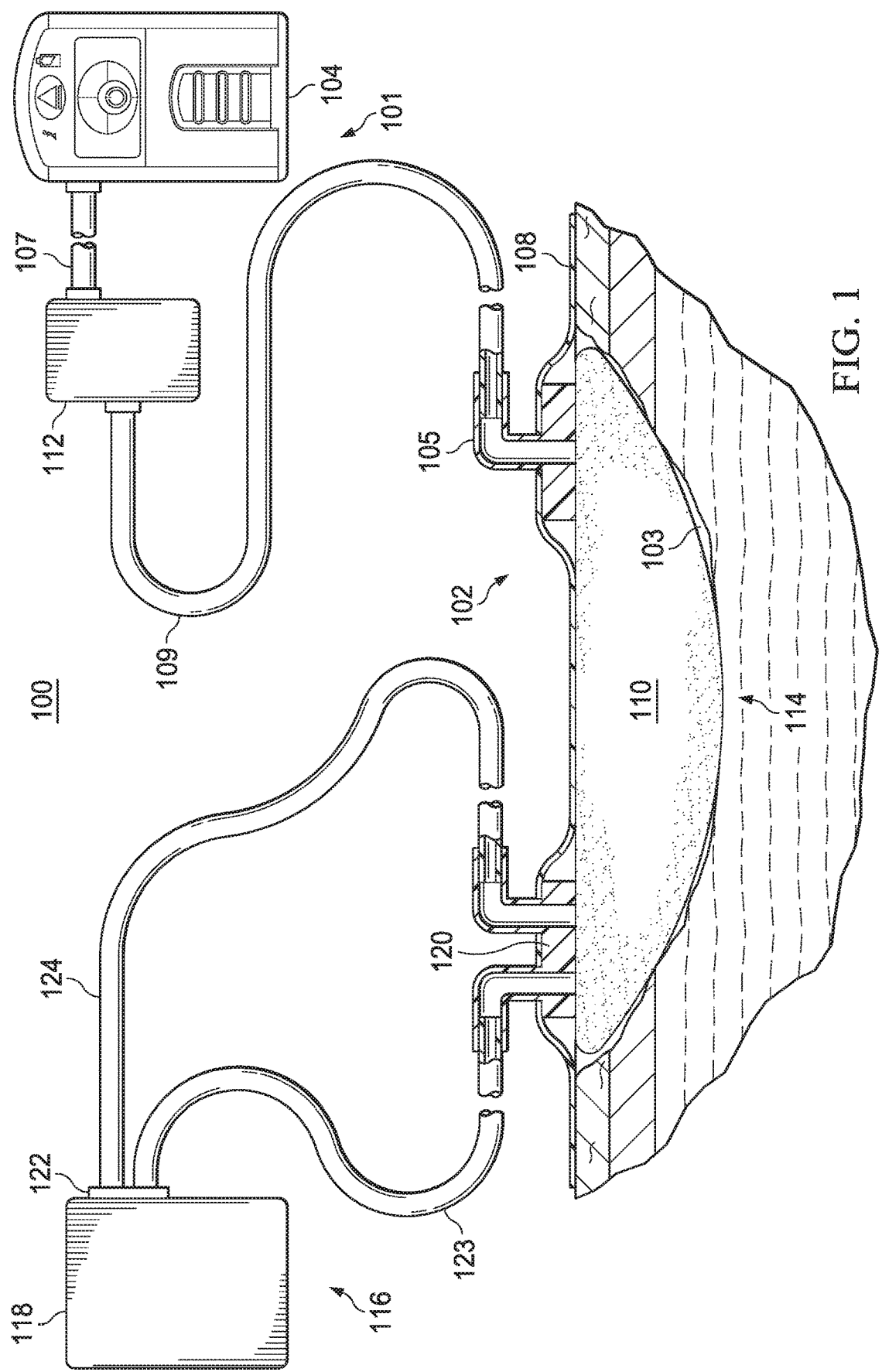
FIG. 1 is a partial sectional view of a reduced-pressure therapy system and an instillation therapy system for treating a tissue site in accordance with this specification.

FIG. 1 is a partial sectional view of a therapy system 100 that may include a reduced-pressure therapy system 101 and an instillation therapy system 116 fluidly coupled to a tissue site 114 in accordance with some embodiments. In an illustrative embodiment, the therapy system 100 may also include a dressing 102 coupled to a tissue site 114. The dressing 102 may include a drape, such as a drape 108, and a tissue interface, such as a manifold 110. The reduced-pressure therapy system 101 may include a reduced-pressure source 104 fluidly coupled to the dressing 102. The reduced-pressure therapy system 101 may also include a fluid container, such as a container 112, fluidly coupled to the dressing 102 and the reduced-pressure source 104 by a reduced-pressure interface 105, a tube 107, and a tube 109. The instillation therapy system 116 may include a fluid source 118 and a fluid interface 120. The fluid source 118 may be fluidly coupled to the fluid interface 120 with a fluid connector 122 and one or more tubes, such as a tube 123 and a tube 124.

A tissue interface, such as the manifold 110, may be placed within, over, on, or otherwise proximate a tissue site, such as the tissue site 114. For example, the manifold 110 may be placed against the tissue site 114, and the drape 108 may be placed over the manifold 110 and sealed to tissue proximate the tissue site 114. Tissue proximate a tissue site is often undamaged epidermis peripheral to the tissue site. Thus, the dressing 102 can provide a sealed therapeutic environment 103 proximate a tissue site. The sealed therapeutic environment 103 may be substantially isolated from the external environment, and the reduced-pressure source 104 can reduce the pressure in the sealed therapeutic environment 103. Reduced pressure applied uniformly through a tissue interface in the sealed therapeutic environment 103 can induce macrostrain and microstrain in a tissue site, as well as remove exudates and other fluids from the tissue site. The removed exudates and other fluids can be collected in the container 112 and disposed of properly.

A "tissue site," such as the tissue site 114, may refer to a wound or defect located on or within tissue including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, reduced pressure may be used in certain tissue areas to grow additional tissue that may be harvested and transplanted to another tissue location.

"Reduced pressure" generally refers to a pressure less than a local ambient pressure, such as the ambient pressure in a local environment external to the sealed therapeutic environment 103 provided by the dressing 102. In many cases, the local ambient pressure may also be the atmospheric pressure at which a patient is located. Alternatively, the pressure may be less than a hydrostatic pressure associated with tissue at a tissue site. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The fluid mechanics of using a reduced-pressure source to reduce pressure in another component or location, such as within the sealed therapeutic environment 103, can be mathematically complex. However, the basic principles of fluid mechanics applicable to reduced-pressure therapy are generally well-known to those skilled in the art, and the process of reducing pressure may be described illustratively herein as "delivering," "distributing," or "generating" reduced pressure, for example.

In general, exudates and other fluids flow toward lower pressure along a fluid path. Thus, the term "downstream" typically implies a position in a fluid path relatively closer to a reduced-pressure source, and conversely, the term "upstream" implies a position relatively further away from a reduced-pressure source. Similarly, it may be convenient to describe certain features in terms of fluid "inlet" or "outlet" in such a frame of reference. This orientation is generally presumed for purposes of describing various features and components of reduced-pressure therapy systems herein. However, the fluid path may also be reversed in some applications (such as by substituting a positive-pressure source for a reduced-pressure source) and this descriptive convention should not be construed as a limiting convention.

A tissue interface, such as the manifold 110, can generally be adapted to contact a tissue site or other layers of a dressing, such as the dressing 102. A tissue interface may be partially or fully in contact with a tissue site. If a tissue site is a wound, for example, a tissue interface may partially or completely fill the wound, or may be placed over the wound. A tissue interface may take many forms, and may have many sizes, shapes, or thicknesses depending on a variety of factors, such as the type of treatment being implemented or the nature and size of a tissue site. For example, the size and shape of a tissue interface may be adapted to the contours of deep and irregular shaped tissue sites.

Generally, a manifold, such as the manifold 110, for example, is a substance or structure adapted to distribute or remove fluids from a tissue site. A manifold may include flow channels or pathways that can distribute fluids provided to and removed from a tissue site. In one illustrative embodiment, the flow channels or pathways may be interconnected to improve distribution of fluids provided to or removed from a tissue site. For example, a manifold may be an open-cell, porous tissue collection, or other porous material such as gauze or felted mat that generally includes structural elements arranged to form flow channels. Liquids, gels, and other foams may also include or be cured to include flow channels.

In one illustrative embodiment, the manifold 110 may be a porous foam pad having interconnected cells adapted to distribute reduced pressure across a tissue site. The foam material may be either hydrophobic or hydrophilic. In one non-limiting example, the manifold 110 may be reticulated polyurethane foam, such as GranuFoam® dressing available from Kinetic Concepts, Inc. of San Antonio, Tex.

In some embodiments, the manifold 110 may be made from a hydrophilic material, and the manifold 110 may also wick fluid away from a tissue site, while continuing to distribute reduced pressure to the tissue site. The wicking properties of the manifold 110 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

A tissue interface may further promote granulation at a tissue site if pressure within a sealed therapeutic environment is reduced. For example, any or all of the surfaces of the manifold 110 may have an uneven, coarse, or jagged profile that can induce microstrains and stresses at the tissue site 114 if reduced pressure is applied to the sealed therapeutic environment 103 through the manifold 110.

In some example embodiments, a tissue interface may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. A tissue interface may further serve as a scaffold for new cell-growth, or a scaffold material may be used in conjunction with the tissue interface to promote cell-growth. In general, a scaffold material may be a biocompatible or biodegradable substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The drape 108 is an example of a sealing member. A sealing member may be constructed from a material that can provide a fluid seal between two components or two environments, such as between a therapeutic environment and a local external environment. A sealing member may be, for example, an impermeable or semi-permeable, elastomeric material that can provide a seal adequate to maintain a reduced pressure at a tissue site for a given reduced-pressure source. For semi-permeable materials, the permeability generally should be low enough that a desired reduced pressure may be maintained. An attachment device may be used to attach a sealing member to an attachment surface, such as undamaged epidermis, a gasket, or another sealing member. An attachment device may take many forms. For example, an attachment device may be a medically-acceptable, pressure-sensitive adhesive that extends about a periphery, a portion, or an entire sealing member. Other example embodiments of an attachment device may include a double-sided tape, paste, hydrocolloid, hydrogel, silicone gel, organogel, or an acrylic adhesive.

In general, components of the reduced-pressure therapy system 101 may be coupled directly or indirectly to each other. For example, the reduced-pressure source 104 may be directly coupled to the container 112 by the tube 107 and indirectly coupled to the dressing 102 through the container 112 and the tube 109. Components may be fluidly coupled to each other to provide a path for transferring fluids (i.e., liquid and/or gas) between the components. In some embodiments, components may be fluidly coupled with a tube, such as the tube 107 or the tube 109, for example. A "tube," as used herein, broadly refers to a tube, pipe, hose, conduit, or other structure with one or more lumina adapted to convey fluids between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material.

Coupling may also include mechanical, thermal, electrical, or chemical coupling (such as a chemical bond) in some contexts.

A reduced-pressure interface, such as the reduced-pressure interface 105 may be a device or component operable to fluidly couple the reduced-pressure source 104 to the dressing 102. In one illustrative embodiment, the reduced-pressure interface 105 may be a T.R.A.C.® Pad or Sensa T.R.A.C.® Pad available from KCI of San Antonio, Tex., modified as described in more detail below. The reduced-pressure interface 105 may fluidly couple the reduced pressure provided by the reduced-pressure source 104 to the manifold 110 through the drape 108. The manifold 110 may distribute the fluid to the sealed therapeutic environment 103. Thus, the reduced-pressure interface 105 allows reduced pressure to be delivered to the sealed therapeutic environment 103. The reduced-pressure interface 105 may be made of a semi-rigid material. In some embodiments, the reduced-pressure interface 105 may be made from a plasticized polyvinyl chloride (PVC), polyurethane, cyclic olefin copolymer elastomer, thermoplastic elastomer, poly acrylic, silicone polymer, or polyether block amide copolymer.

A reduced-pressure source, such as the reduced-pressure source 104, may be a reservoir of air at a reduced pressure, or may be a manual or electrically-powered device that can reduce the pressure in a sealed volume, such as a vacuum pump, a suction pump, a wall suction port available at many healthcare facilities, or a micro-pump, for example. The reduced-pressure source may be housed within or used in conjunction with other components, such as sensors, processing units, alarm indicators, memory, databases, software, display devices, or user interfaces that further facilitate reduced-pressure therapy. While the amount and nature of reduced pressure applied to a tissue site may vary according to therapeutic requirements, the pressure typically ranges between about −5 mm Hg (−667 Pa) and about −500 mm Hg (−66.7 kPa). Common therapeutic ranges are between about −75 mm Hg (−9.9 kPa) and about −300 mm Hg (−39.9 kPa).

A "container," such as the container 112, may broadly include a canister, pouch, bottle, vial, or other fluid collection apparatus. A container can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with reduced-pressure therapy.

A fluid source, such as the fluid source 118, may be a reservoir of fluid at an atmospheric or greater pressure, or may be a manual or electrically-powered device, such as a pump, that can convey fluid to a sealed volume, such as the sealed therapeutic environment 103, for example. A fluid source may be housed within or used in conjunction with other components, such as sensors, processing units, alarm indicators, memory, databases, software, display devices, or user interfaces that further facilitate instillation therapy. The amount and nature of the fluid applied to a tissue site may vary according to therapeutic requirements, which may include the size of the sealed therapeutic environment, the type of fluid, and any additives to the fluid. In some embodiments, the fluid may include: hypochlorite based solutions, such as hypochlorous acid and sodium hypochlorite; silver nitrate; sulfur based solutions, such as sulfonamides; biguanides, such as polyhexanide; cationic solutions, such as octenidine and benzalkonium chloride; and isotonic solutions.

A fluid interface, such as the fluid interface 120 may be a device or component operable to fluidly couple the fluid source 118 to the dressing 102. The fluid interface 120 may fluidly couple the fluid provided by the fluid source 118 to the manifold 110 through the drape 108. The manifold 110 may distribute the fluid to the sealed therapeutic environment 103. Thus, the fluid interface 120 allows fluid to be delivered to the sealed therapeutic environment 103. In some embodiments, the fluid interface 120 may also fluidly couple the fluid source 118 to the manifold 110 to determine a pressure at the tissue site 114. In some embodiments, the fluid interface 120 may couple two tubes, such as the tube 124 and the tube 123 to the manifold 110. The fluid interface 120 may be made of a semi-rigid material. In some embodiments, the fluid interface 120 may be made from a plasticized polyvinyl chloride (PVC), polyurethane, cyclic olefin copolymer elastomer, thermoplastic elastomer, poly acrylic, silicone polymer, or polyether block amide copolymer.

A fluid connector, such as the fluid connector 122, may be a device or component configured to couple the tube 124 and the tube 123 to the fluid source 118. A fluid connector may fluidly couple one or more tubes to one or more components of a fluid source. In some embodiments, a fluid connector may fluidly couple a multi-lumen tube to one or more components of a fluid source. In some embodiments, a fluid connector may also be releasably coupled to a fluid source so that the fluid connector may be discarded after use of the fluid connector 122. In some embodiments, a fluid connector may be a device permanently attached to a fluid source.

In general, components of the instillation therapy system 116 may be coupled directly or indirectly to each other. For example, the fluid source 118 may be directly coupled to the fluid interface 120 and indirectly coupled to the dressing 102 through the fluid interface 120. Components may be fluidly coupled to each other to provide a path for transferring fluids (i.e., liquid and/or gas) between the components. In some embodiments, components may be fluidly coupled with a tube, for example the tube 123 or the tube 124. In some embodiments, the tube 123 and the tube 124 may be single-lumen conduits having a central flow passage extending through each tube.

In operation, the reduced-pressure therapy system 101 may provide reduced pressure to the sealed therapeutic environment 103 through the reduced-pressure interface 105. Fluid, including exudates and other liquids, may be drawn from the tissue site 114 through the manifold 110 and into the reduced-pressure interface 105. Similarly, the instillation therapy system 116 may provide fluids to the sealed therapeutic environment 103 through the fluid interface 120. Fluid, including therapeutic liquids, may flow from the fluid source 118, through the tube 124 and into the sealed therapeutic environment 103 through the fluid interface 120. The fluids may be distributed to the tissue site 114 by the manifold 110.

In some embodiments, the reduced-pressure therapy system 101 and the instillation therapy system 116 may operate concurrently. If the reduced-pressure therapy system 101 and the instillation therapy system 116 operate concurrently, the fluid interface 120 and the reduced-pressure interface 105 may be positioned to maximize the distance between them. For example, if the tissue site 114 is elongated and includes two opposing ends, the fluid interface 120 and the reduced-pressure interface 105 may be positioned proximate the opposing ends. If the tissue site 114 is generally circular, the fluid interface 120 and the reduced-pressure interface 105 may be placed proximate opposing ends of a diameter of the tissue site 114. Fluid may flow from the fluid interface 120 through the sealed therapeutic environment 103 to the reduced-pressure interface 105. In some embodiments, the reduced pressure supplied through the reduced-pressure interface 105 may aid in the distribution of fluids provided through the fluid interface 120.

In some embodiments, the reduced-pressure therapy system 101 and the instillation therapy system 116 may not operate concurrently. In these embodiments, the instillation therapy system 116 may provide fluid to the sealed therapeutic environment 103 while the reduced-pressure therapy system 101 is not providing reduced pressure. The fluid source 118 may include a pump that may move the fluid to the manifold 110 for distribution to the tissue site 114. The fluid may remain in the sealed therapeutic environment 103 until the operation of the reduced-pressure therapy system 101. If the reduced-pressure therapy system 101 provides reduced pressure, the reduced-pressure therapy system 101 may draw the fluid from the sealed therapeutic environment 103 into the container 112.

Figure 2:
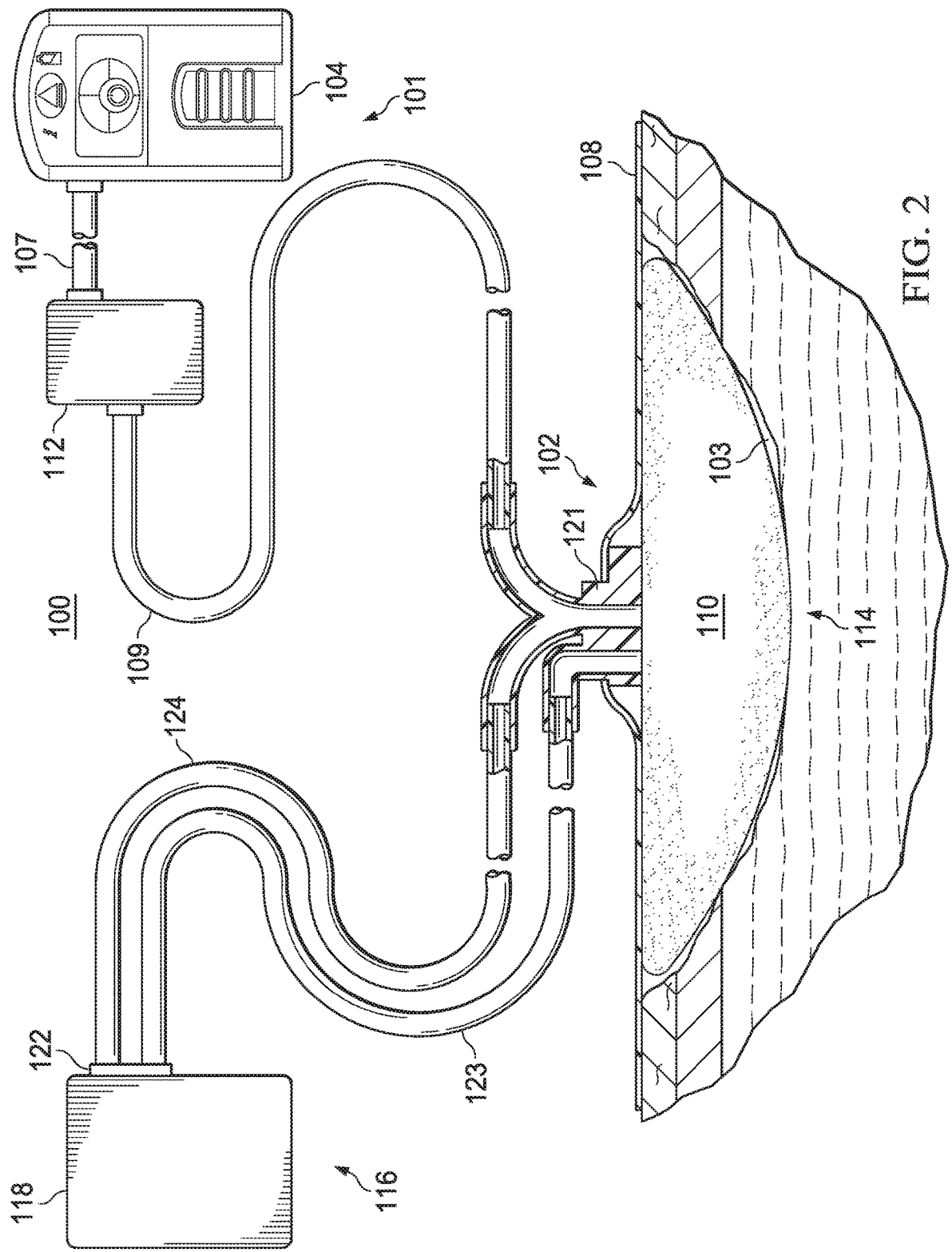
FIG. 2 is a partial sectional view of another embodiment of the reduced-pressure therapy system and the instillation therapy system for treating a tissue site in accordance with an illustrative embodiment.

FIG. 2 is a partial sectional view of the reduced-pressure therapy system 101 and the instillation therapy system 116 illustrating additional details that may be associated with some embodiments. In some embodiments, the fluid interface 120 and the reduced-pressure interface 105 may be combined into a dressing interface 121. As shown in FIG. 2, the dressing interface 121 maybe coupled to the dressing in a manner similar to the fluid interface 120 and the reduced-pressure interface 105. The dressing interface 121 may be configured to receive the tube 123, the tube 124, and the tube 109 and provide a fluid coupling through the drape 108 to the tissue site 114 and the sealed therapeutic environment 103.

In some embodiments, the dressing interface 121 may be similar to and operate as described in U.S. patent application Ser. No. 13/009,220, by Locke, et al., entitled "Wound-Connection Pads for Fluid Instillation and Negative Pressure Wound Therapy, and Systems and Methods," filed Jan. 19, 2011, which is incorporated by reference herein for all purposes. The dressing interface 121 may fluidly couple the fluid provided by the fluid source 118 and the reduced pressure provided by the reduced-pressure source 104 to the manifold 110 through the drape 108. The dressing interface 121 may be made of a semi-rigid material. In some embodiments, the dressing interface 121 may be made from a plasticized polyvinyl chloride (PVC), polyurethane, cyclic olefin copolymer elastomer, thermoplastic elastomer, poly acrylic, silicone polymer, or polyether block amide copolymer. In the embodiment of FIG. 2, operation of the instillation therapy system 116 and the reduced-pressure therapy system 101 may alternate. The instillation therapy system 116 may provide fluid through the dressing interface 121 while the reduced-pressure therapy system 101 is not operating, and the reduced-pressure therapy system 101 may provide reduced-pressure through the dressing interface 121 while the instillation therapy system 116 is not operating.

Figure 3:
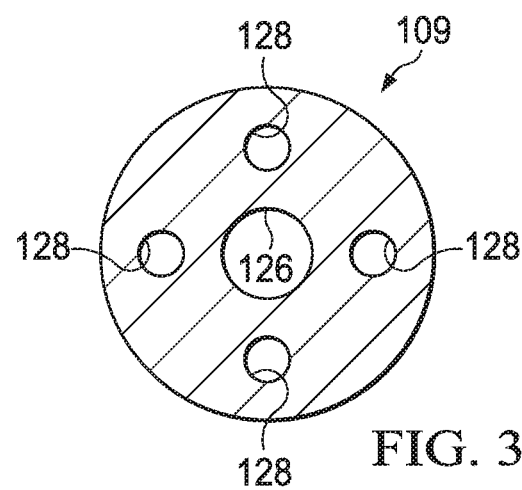
FIG. 3 is a sectional view of a tube for fluidly coupling a reduced-pressure source to a reduced-pressure interface in accordance with an illustrative embodiment.

FIG. 3 is a sectional view of the tube 109 illustrating additional details that may be associated with some embodiments of the reduced-pressure therapy system 101. As shown, the tube 109 may be a multi-lumen tube. In the illustrative embodiment, the tube 109 may include at least one primary lumen 126 and one or more secondary lumens 128. In some embodiments, the tube 109 includes four secondary lumens 128. The tube 109 may have different shapes and include more or fewer primary lumens 126 and secondary lumens 128. The primary lumen 126 may provide a path between the reduced-pressure source 104 and the reduced-pressure interface 105 for delivery of reduced pressure. The secondary lumens 128 may function as sensing lumens. In some embodiments, the secondary lumens 128 may fluidly communicate pressure at a terminal end of the tube 109 within the reduced-pressure interface 105 to the reduced-pressure source 104. The secondary lumens 128 may be fluidly isolated from the primary lumen 126 so as not to interfere with the process of sensing the pressure. The pressure communicated by the secondary lumens 128 may be representative of the pressure at the tissue site 114. Referring back to FIG. 1 and FIG. 2, the tube 123 and the tube 124 may be combined into a multi-lumen tube, similar to the tube 109, each having at least one primary lumen, similar to the primary lumens 126 of the tube 109, and one or more secondary lumens, similar to the secondary lumens 128 of the tube 109. If the tube 123 and the tube 124 are combined into a multi-lumen tube, the secondary lumens may be fluidly coupled between the tissue site 114 and the fluid source 118 to sense pressure at the tissue site 114. The primary lumens would deliver instillation fluid to the tissue site 114. Referring more specifically to FIG. 2, the pressure being sensed by the tube 123 may be replaced by the secondary lumens 128 if the tube 124 is a multi-lumen tube.

Reduced-pressure therapy has been shown to improve healing of tissue sites. Similarly, instillation therapy has been shown to improve the healing of tissue sites. Furthermore, tissue sites treated with both reduced-pressure therapy and instillation therapy have been shown to have improved healing over the use of reduced-pressure therapy or instillation therapy alone. Current systems providing both reduced-pressure therapy and instillation therapy are complex and difficult to properly administer to a tissue site. In addition, the systems may be quite expensive, which may pose problems for the use of such systems in some locations, in particular, in locations where health care services may not be readily available. Some systems provide both reduced-pressure therapy and instillation therapy without the complexity and cost involved in combined systems; however, these systems may be labor intensive and require significant clinician involvement for the proper administration of therapy. For example, in some systems providing both reduced-pressure therapy and instillation therapy, the reduced-pressure therapy system may be coupled to the tissue site, and a clinician may use a syringe to administer fluids to the tissue site through the dressing. Administering fluids with a syringe requires the clinician to actively monitor the dressing and the fluid application to prevent inadvertent over application of fluids. As it may be difficult to see the tissue site through the sealing member, a clinician may find it difficult to accurately determine the appropriate initiation and termination of instillation therapy.

As disclosed herein, the instillation therapy system 116 can overcome these shortcomings and others by providing an instillation therapy system that may monitor the delivery of reduced pressure to a tissue site by a reduced-pressure system, and in response, the instillation therapy system may provide fluids in response to the reduced-pressure therapy. For example, in some embodiments of the instillation therapy system 116, the instillation therapy system 116 may monitor a pressure in the sealed therapeutic environment 103 and, in response, administer fluids in accordance with the administration of reduced pressure by the reduced-pressure therapy system 101.

Figure 4:
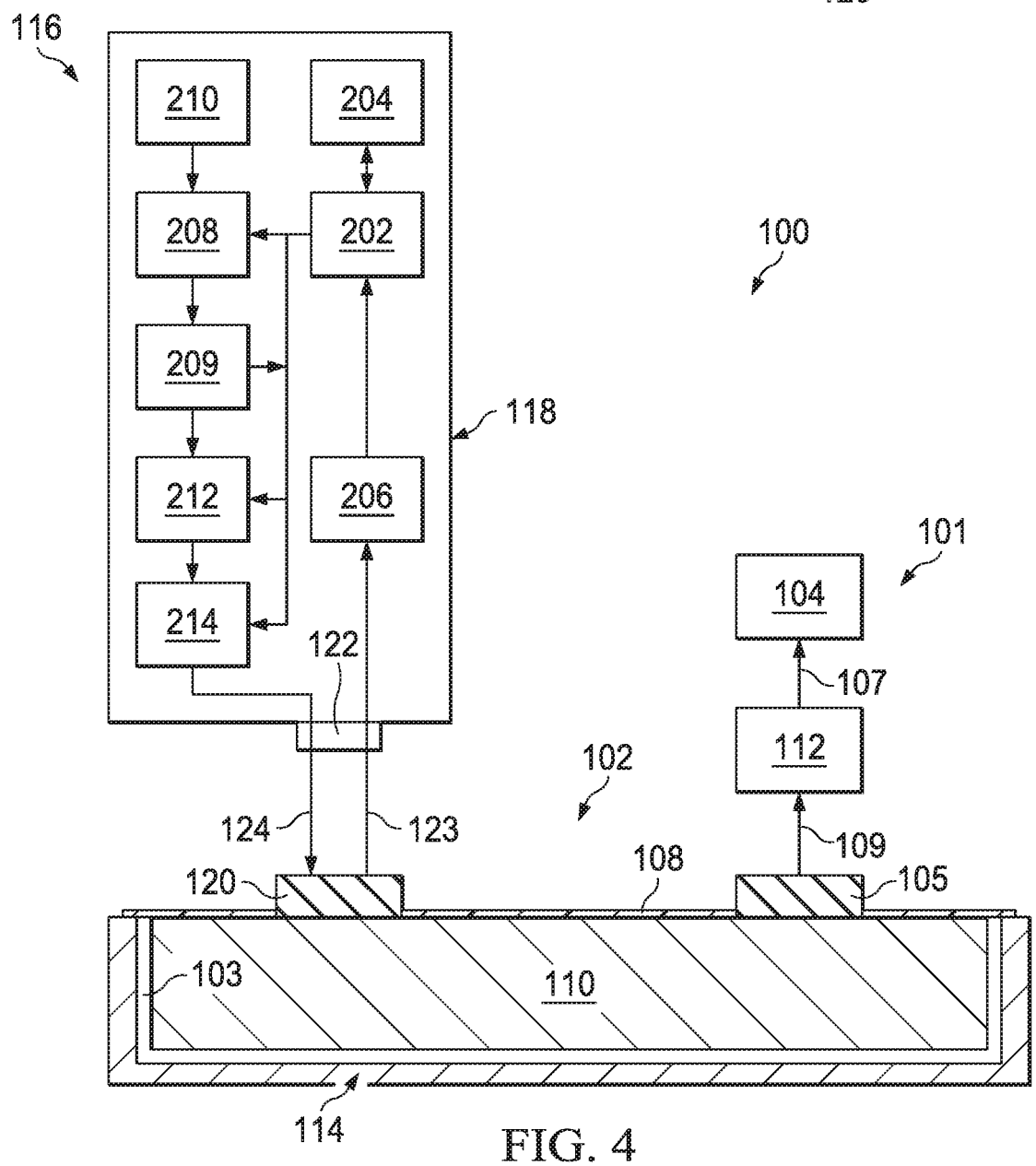
FIG. 4 is a schematic diagram of the reduced-pressure therapy system and the instillation therapy system in accordance with an illustrative embodiment.

FIG. 4 is a schematic diagram of the therapy system 100 illustrating additional details that may be associated with some embodiments of the instillation therapy system 116. In some embodiments, the fluid source 118 may include a controller 202, a user interface 204, and a sensor 206. The user interface 204 and the sensor 206 may each be communicatively coupled to the controller 202. As used herein, communicative coupling may refer to a coupling between components that permits the transmission of signals between the components. In some embodiments, the signals may be discrete or continuous signals. A discrete signal may be a signal representing a value at a particular instance in a time period. A plurality of discrete signals may be used to represent a changing value over a time period. A continuous signal may be a signal that provides a value for each instance in a time period. The signals may also be analog signals or digital signals. An analog signal may be a continuous signal that includes a time varying feature that represents another time varying quantity. A digital signal may be a signal composed of a sequence of discrete values.

In some embodiments, the communicative coupling between the controller 202, the user interface 204, and the sensor 206 may be one-way communication. In one-way communication, signals may only be sent in one direction. For example, the sensor 206 may generate a signal that may be communicated to the controller 202, but the controller 202 may not be capable of sending a signal to the sensor 206. In some embodiments, the communicative coupling between the controller 202, the user interface 204, and the sensor 206 may be two-way communication. In two-way communication, signals may be sent in both directions. For example, the controller 202 and the user interface 204 may be communicatively coupled so that the controller 202 may send and receive signals from the user interface 204. Similarly, the user interface 204 may send and receive signals from the controller 202. In some embodiments, signal transmission between the controller 202 and another device, such as the user interface 204, may be referred to as the controller 202 operating the device.

The controller 202 may be a computing device or system, such as a programmable logic controller, a data processing system, or the like. In other embodiments, the controller 202 may be configured to receive input from the sensor 206. In some embodiments, the controller 202 is configured to receive input from both the user interface 204 and the sensor 206. In some embodiments, the controller 202 may receive input, such as an electrical signal, from an alternative source, such as through an electrical port, for example. In some embodiments, the controller 202 may be a data processing system. A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code in order to reduce the number of times code is retrieved from bulk storage during execution.

In some embodiments, the controller 202 may be a programmable logic controller ("PLC"). A PLC may be a digital computer configured to receive one or more inputs and send one or more outputs in response to the one or more inputs. A PLC may include a non-volatile memory configured to store programs or operational instructions. In some embodiments, the non-volatile memory may be operationally coupled to a battery-back up so that the non-volatile memory retains the programs or operational instructions if the PLC otherwise loses power. In some embodiments, a PLC may be configured to receive discrete signals and continuous signals and produce discrete and continuous signals in response.

A user interface, such as the user interface 204, may be a device configured to allow communication between the controller 202 and an environment external (external environment) to the fluid source 118. In some embodiments, an external environment may include an operator or a computer system configured to interface with the fluid source 118, for example. In some embodiments, a user interface may receive a signal from a controller and present the signal in a manner that may be understood by an external environment. In some embodiments, a user interface may receive signals from an external environment and, in response, send signals to a controller. A controller may process the signals received from a user interface and take further action. In some embodiments, a user interface may be a graphical user interface, a touchscreen, or one or more motion tracking devices. A user interface may also include one or more display screens, such as a liquid crystal display ("LCD"), lighting devices, such as light emitting diodes ("LED") of various colors, and audible indicators, such as a whistle, configured to emit a sound that may be heard by an operator. A user interface may further include one or more devices, such as knobs, buttons, keyboards, remotes, touchscreens, ports that may be configured to receive a discrete or continuous signal from another device, or other similar devices; these devices may be configured to permit the external environment to interact with the user interface 204.

A pressure sensor, such as the sensor 206, may be a piezoresistive strain gauge, a capacitive sensor, an electromagnetic sensor, a piezoelectric sensor, an optical sensor, or a potentiometric sensor, for example. In some embodiments, a pressure sensor can measure a strain caused by an applied pressure. A pressure sensor may be calibrated by relating a known amount of strain to a known pressure applied. The known relationship may be used to determine an unknown applied pressure based on a measured amount of strain. In some embodiments, a pressure sensor may include a receptacle configured to receive an applied pressure. In an illustrative embodiment, the sensor 206 may be fluidly coupled to the fluid interface 120 by the tube 123 to receive a pressure from the tube 123.

The fluid source 118 may also include a valve 208, a flow meter 209, and a fluid reservoir 210. In some embodiments, the valve 208 may be communicatively coupled to the controller 202, and the valve 208 may be further fluidly coupled between the fluid reservoir 210 and the fluid interface 120. A valve, such as the valve 208, may be a device configured to selectively permit fluid flow through the valve. A valve may be a ball valve, a gate valve, a butterfly valve, or other valve type that may be operated to prevent or permit fluid flow through the valve. Generally, a valve may include a valve body having a flow passage, a valve member disposed in the flow passage and operable to selectively block the flow passage, and an actuator configured to operate the valve member. An actuator may be configured to position the valve member in a closed position, preventing fluid flow through the flow passage of the valve, an open position, permitting fluid flow through the fluid passage of the valve, or a metering position, permitting fluid flow through the flow passage of the valve at a selected flow rate. In some embodiments, the actuator may be a mechanical actuator configured to be operated by an operator. In some embodiments, the actuator may be an electromechanical actuator configured to be operated in response to the receipt of a signal input. For example, the actuator may include an electrical motor configured to receive a signal from a controller, such as the controller 202. In response to the signal, the electrical motor of the actuator may move the valve member of the valve. In some embodiments, the valve 208 may be configured to selectively permit fluid communication between the fluid reservoir 210 and the fluid interface 120 in response to a signal from the controller 202. In this context, the controller 202 may be referred to as: operating the valve; placing the valve 208 in an open position, a closed position, or a metering position; and opening the valve 208, closing the valve 208, or metering the valve 208.

In some embodiments, the flow meter 209 may be communicatively coupled to the controller 202, and the flow meter 209 may be further fluidly coupled between the valve 208 and the fluid interface 120. A flow meter, such as the flow meter 209, may be a device configured to determine a fluid flow rate. A flow meter may include a mechanical flow meter, a pressure based flow meter, an optical flow meter, an open channel flow meter, a thermal mass flow meter, a vortex flow meter, electromagnetic, ultrasonic and coriolis flow meters, and laser doppler flow meters. The flow meter 209 may determine a rate of fluid flow through the valve 208 and transmit a signal to the controller 202 corresponding to the determined flow rate. The controller 202 may receive the determined flow rate and determine a total volume of fluid delivered in response.

A fluid reservoir, such as the fluid reservoir 210, may be a container for storing or holding fluid. A fluid reservoir may broadly include a canister, pouch, bottle, vial, or other fluid storage apparatus. A fluid reservoir can be used to manage fluid to be delivered to a tissue site. In many environments, a rigid fluid reservoir may be preferred or required for storing and delivering of fluids. In other environments, fluids may be properly stored and delivered without a rigid fluid reservoir. In some embodiments, a fluid reservoir may be a device that is integrated into a fluid source. For example, the fluid reservoir 210 may be an integral component of the fluid source 118. In other embodiments, a fluid reservoir may be a removable component of a fluid source. For example, the fluid reservoir 210 may be removable from the fluid source 118. In still other embodiments, a fluid reservoir may be a separate component from a fluid source that may be fluidly coupled to the fluid source. For example, the fluid reservoir 210 may be a separate device that may be fluidly coupled by a tube to the fluid source 118.

In some embodiments, the valve 208 may be fluidly coupled to the fluid interface 120 through the tube 124. Operation of the valve 208 may permit fluid to flow from the fluid reservoir 210 through the tube 124 into the fluid interface 120, where the fluid may be distributed by the manifold 110.

In some embodiments, the sensor 206 may be fluidly coupled to the fluid interface 120 through the tube 123. In some embodiments, the tube 123 may fluidly communicate a pressure at the fluid interface 120 to the sensor 206. In some embodiments, the pressure at the fluid interface 120 may be representative of a pressure in the sealed therapeutic environment 103. In some embodiments, the sensor 206 may be an electronic strain gauge sensor that is incorporated into the fluid interface 120. The strain gauge may have a thin piezoresistive film on the drape of the pad which deforms under pressure. The deformation may indicate the pressure in the sealed therapeutic environment 103. In some embodiments, the fluid interface 120 may be communicatively coupled to the controller 202 so that the controller 202 may receive a signal from the strain gauge.

In some embodiments, the fluid source 118 may include an instillation pump 212. The instillation pump 212 may be fluidly coupled between the valve 208 and the fluid interface 120 and communicatively coupled to the controller 202. The instillation pump 212 may be operated by the controller 202 in a manner similar to the operation of the valve 208 to provide fluid to the fluid interface 120 and the sealed therapeutic environment 103. In other embodiments, the instillation pump 212 may replace the valve 208. In some embodiments, the instillation pump 212 may be configured to pre-charge a dosage of fluid for delivery to the tissue site 114. For example, the instillation pump 212 may be configured to pressurize a dosage of fluid prior to delivery of fluids so that the fluids may be delivered to the tissue site 114. A dosage of fluid may be the volume of fluid prescribed by a caregiver to treat the tissue site 114 during a cycle of instillation therapy.

In some embodiments, the fluid source 118 may also include an instillation sensor 214. The instillation sensor 214 may be fluidly coupled to the tube 124 and communicatively coupled to the controller 202. In some embodiments, the controller 202 may monitor pressure in the tube 124 with the instillation sensor 214. In the event that the instillation sensor 214 sends a signal that deviates from the signal received from the sensor 206, the controller 202 may operate the user interface 204 to indicate a blockage or a leak condition.

In operation, the sensor 206 may determine the pressure in the fluid interface 120. As previously described, the pressure in the fluid interface 120 may be representative of the pressure in the sealed therapeutic environment 103. The controller 202 may receive the signal sent by the sensor 206, and in response, the controller 202 may operate the valve 208 and the user interface 204. In some embodiments, the controller 202 may determine that the valve 208 should be in the open position in response to the signal received from the sensor 206. The controller 202 may transmit a signal to the valve 208 to cause the valve 208 to actuate and move from the metering or the closed position to the open position. If the valve 208 is positioned in the open position, fluid may flow from the fluid reservoir 210 into the sealed therapeutic environment through the valve 208, the tube 124, and the fluid interface 120.

In some embodiments, the controller 202 may also generate and send a signal to the user interface 204 in response to the signal from the sensor 206. For example, the controller 202 may receive a signal from the sensor 206 corresponding to a particular pressure in the fluid interface 120. In response, the controller 202 may generate and send a signal to the user interface 204. The user interface 204 may receive the signal and, in response, provide a visual or auditory output that may be understood by the external environment. For example, in some embodiments, the user interface 204 may be an LCD. The user interface 204 may receive a signal corresponding to a particular pressure in the fluid interface 120 from the controller 202. The user interface 204 may display the signal on the LCD as a numerical representation of the particular pressure at the fluid interface 120.

In some embodiments, the controller 202 may include operational instructions permitting the controller 202 to operate the valve 208 to provide instillation therapy. In some embodiments, the controller 202 may operate the valve 208 in a constant mode. In the constant mode, the fluid source 118 may deliver fluids to the fluid interface 120 without adjustment in response to conditions external to the fluid source 118. For example, the controller 202 may receive a signal from the user interface 204 that corresponds to a selection of the constant mode. In response, the controller 202 may send a signal to the valve 208, placing the valve 208 in the open position. Fluid may flow freely from the fluid reservoir 210 to the fluid interface 120. In some embodiments, the controller 202 may receive a signal from the user interface 204 that corresponds to a selection of the constant mode at a selected flow rate. In response, the controller 202 may send a signal to the valve 208 instructing the valve 208 to move to a metering position corresponding to the selected flow rate. Fluid may flow from the fluid reservoir 210 to the fluid interface 120 at the selected flow rate.

In some embodiments, the controller 202 may operate the valve 208 in an intermittent mode. In the intermittent mode, the fluid source 118 may deliver fluid to the tissue site 114 in discrete time periods independent of conditions external to the fluid source 118. For example, the fluid source 118 may provide fluids for a period of one minute followed by a period of one minute where the fluid source 118 provides no fluids. In some embodiments, the controller 202 may receive a signal from the user interface 204 corresponding to a selection of the intermittent mode. In some embodiments, the controller 202 may include pre-determined time periods for a duration of fluid delivery and an interval between fluid delivery for the intermittent mode. In some embodiments, the signal from the user interface 204 may also provide a duration of fluid delivery and a duration of no delivery. In response, the controller 202 may send a signal to the valve 208 to move the valve 208 to the open position, providing fluids and initiating the duration of fluid delivery. When the duration of fluid delivery ends, the controller 202 may send a signal to the valve 208 to move the valve 208 to the closed position, blocking fluid flow and initiating the interval between fluid delivery. When the interval between fluid delivery ends, the controller 202 may send a signal to the valve 208 to move the valve 208 to the open position, providing fluid and initiating the duration of fluid delivery. Opening and closing of the valve 208 may repeat until the instillation therapy concludes. In some embodiments, the controller 202 may receive a signal from the user interface 204 corresponding to a selection of the intermittent mode and a selected flow rate. In response, the controller 202 may send a signal to the valve 208 to move the valve to a metering position corresponding to the selected flow rate during the duration of fluid delivery. In other embodiments, the controller 202 may operate the instillation pump 212 to control the delivery of fluids during the duration of fluid delivery and the interval between fluid delivery.

In some embodiments of the intermittent mode, the controller 202 may monitor the flow rate through the valve 208 with the flow meter 209. The controller 202 may operate the valve 208 in response to a total volume of fluid flow through the valve 208. For example, the controller 202 may operate the valve 208, placing the valve 208 in an open position. The controller 202 my monitor the flow rate with the flow meter 209, determining the total volume of fluid delivered while the valve 208 is in the open position. If the total volume of fluid delivered reaches a predetermined total volume of fluid to be delivered, also referred to as a dosage of fluid, the controller 202 may operate the valve 208, moving the valve 208 to the closed position.

In some embodiments, the controller 202 may operate the valve 208 in a dynamic mode. During the dynamic mode, the controller 202 may coordinate the delivery of instillation fluid with the delivery of reduced pressure by a reduced-pressure source. For example, the controller 202 may open the valve 208 when reduced pressure is still present in the sealed therapeutic environment 103, which draws fluid from the fluid reservoir 210, through the valve 208 and into the sealed therapeutic environment 103. Using the reduced pressure in a sealed therapeutic environment to draw fluid from the fluid reservoir 210 may simultaneously decrease the reduced pressure in the sealed therapeutic environment 103. As the reduced pressure decreases in the sealed therapeutic environment 103, the rate of fluid flow from the fluid reservoir 210 may also slow down. If the pressure in the sealed therapeutic environment 103 and the ambient pressure proximate the fluid reservoir 210 are approximately the same, fluid flow from the fluid reservoir 210 may stop, thereby avoiding over-pressurizing the sealed therapeutic environment 103 with the instillation fluids. In some embodiments, the controller 202 may monitor the volume of fluid flow through the valve 208 with the flow meter 209. If a predetermined dosage of fluid has been delivered prior to the sealed therapeutic environment 103 reaching ambient pressure, the controller 202 may close the valve 208.

In the dynamic mode, the fluid source 118 may provide fluids to the fluid interface 120 in response to operation of the reduced-pressure therapy source 104. In some embodiments, the controller 202 may be programmed to open the valve 208 in response to a particular pressure that may be detected by the sensor 206. In some embodiments, the particular pressure may also be referred to as a trigger pressure ($P_t$). Generally, if the signal from the sensor 206 corresponds with a pressure that is about equal to the trigger pressure ($P_t$) following a period of generally static or steady-state reduced pressure, the controller 202 may open the valve 208 in response. If the trigger pressure ($P_t$) is less than an ambient pressure proximate the fluid reservoir 210, (that is, the trigger pressure ($P_t$) is a greater reduced-pressure than the ambient pressure), that reduced pressure draws instillation fluid from the fluid reservoir 210 through the valve 208 to the fluid interface 120. In some embodiments, the controller 202 may position the valve 208 in a metering position in response to the trigger pressure ($P_t$), permitting fluid flow at predefined flow rates.

Figure 5:
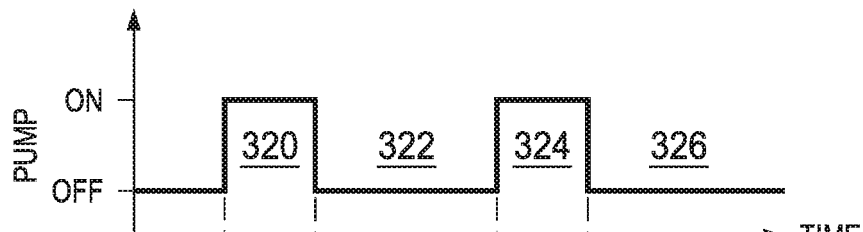
FIG. 5 is a graphical depiction of the operation of the reduced-pressure therapy system of FIG. 4 in accordance with an illustrative embodiment.
Figure 6A:
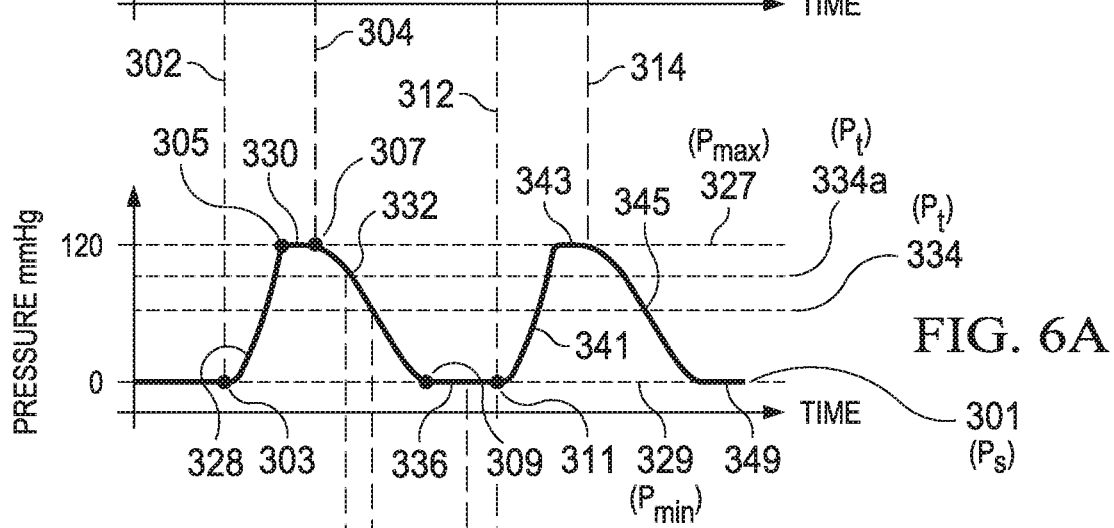
FIG. 6A is a graphical depiction of a pressure profile of reduced-pressure provided to the tissue site by the reduced-pressure therapy system of FIG. 4 in accordance with an illustrative embodiment.
Figure 7:
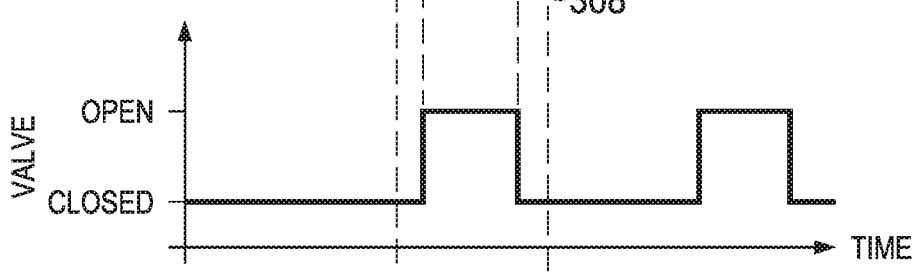
FIG. 7 is a graphical depiction of the operation of a valve of the fluid source of FIG. 4 in accordance with an illustrative embodiment.
Figure 8:
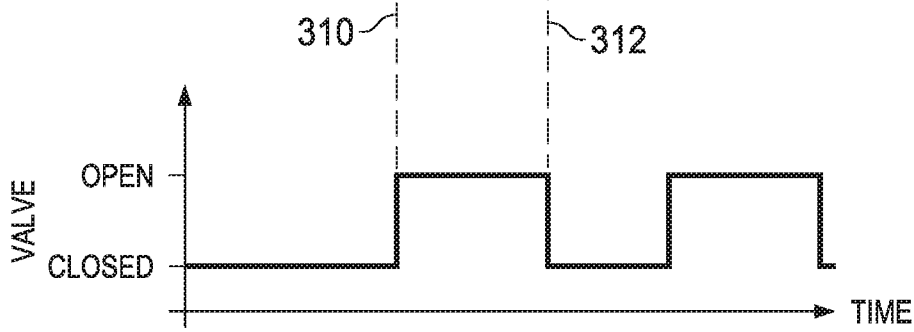
FIG. 8 is a graphical depiction of the operation of the valve of the fluid source of FIG. 4 in accordance with another illustrative embodiment.

Further detailed operation of the dynamic mode may be described with respect to FIG. 4, FIG. 5, FIG. 6A, FIG. 7, and FIG. 8. FIG. 5 is a graphical representation of the operation of the reduced-pressure therapy system 101 that may be associated with some embodiments. In FIG. 5, the y-axis represents the operating state of the reduced-pressure therapy system 101, which may be either in an "on-state" or an "off-state," and the x-axis represents time. FIG. 6A is a graphical representation of a pressure profile 301 ($P_s$) of the sealed therapeutic environment 103 as measured at the sensor 206 that may be associated with some embodiments. In FIG. 6A, the y-axis represents the absolute value of the reduced pressure measured by the sensor 206 at the fluid interface 120, and the x-axis represents time. As previously described, the reduced pressure measured at the fluid interface 120 may be representative of the reduced pressure in the sealed therapeutic environment 103 formed by the tissue site 114 and the drape 108. FIG. 7 is a graphical representation of the operation of the valve 208 that may be associated with some embodiments. In FIG. 7, the y-axis represents the position of a valve member of the valve 208, which may be in an open position or a closed position in response to the pressure profile 301 ($P_s$), and the x-axis represents time. FIG. 8 is a graphical representation of the operation of the valve 208 that may be associated with other embodiments. In FIG. 8, the y-axis represents the position of a valve member of the valve 208, which may be in an open position or a closed position in response to the pressure profile 301 ($P_s$), and the x-axis represents time.

Some or all of FIGS. 5, 6A, 7, and 8 include a reference line 302, a reference line 304, a reference line 306, a reference line 308, a reference line 310, a reference line 312, and a reference line 314. The reference lines 302-314 are positioned at the same location of the x-axis in each figure in which the reference lines appear. Thus, the reference lines 302, 304, 306, 308, 310, 312, and 314 align FIG. 5, FIG. 6A, FIG. 7, and FIG. 8 to relate the operation of the reduced-pressure source 104 and the fluid source 118 based on the conditions in the sealed therapeutic environment 103.

In some embodiments, the reduced-pressure therapy system 101 may be operating in an intermittent mode so that reduced-pressure may be supplied to the sealed therapeutic environment 103 in discrete time increments. As shown in FIG. 5, in the intermittent mode of operation, the reduced-pressure source 104 may have a time period in which the reduced-pressure source 104 is operating to provide reduced pressure, such as during "on-state." The reduced-pressure source 104 may also have a time period in which the reduced-pressure source 104 is not providing reduced pressure, such as during an "off-state." As described with respect to FIG. 5, the on-state represents operation of a pump or other device in the reduced-pressure source 104 to provide reduced pressure to the sealed therapeutic environment 103. The off-state represents a time period in which the reduced-pressure source 104 may be powered on, but it is not providing reduced-pressure to the sealed therapeutic environment 103.

As shown in FIG. 5, the reduced-pressure source 104 may be turned on at the reference line 302. The reduced-pressure source 104 may be turned off at the reference line 304. Thus, the reduced-pressure source 104 is in an "on-state" 320 between the reference line 302 and the reference line 304 and in an "off-state" 322 between the reference line 304 and the reference line 312. The reduced-pressure source 104 may be turned on at the reference line 312. The reduced-pressure source 104 may be turned off at the reference line 314. Thus, the reduced-pressure source 104 is in an "on-state" 324 between the reference line 312 and the reference line 314 and in an "off-state" 326 after the reference line 314. In FIG. 5, the graph representing operation of the reduced-pressure source 104 forms a square wave having a duty cycle represented as the ratio between the off-state 322 and the on-state 320. In some embodiments, the off-state 322 may be twice as long as the on-state 320, that is, a duty cycle or ratio of the off-state 322 to the on-state 320 is 2/1. In other embodiments, the duty cycle may be 1/1, 3/1, 4/1, or other similar ratios.

FIG. 6A may illustrate the pressure profile 301 ($P_s$) associated with the pressure at the fluid interface 120. In an illustrative embodiment, the absolute value of the pressure may range from about 0 mm Hg to about 120 mm Hg gauge pressure. As described herein, pressure at about 0 mm Hg may be referred to as an atmospheric pressure or minimum pressure ($P_{min}$), as shown by the dashed line 329. Reduced-pressure at about 120 mm Hg may be referred to as a therapy pressure. The therapy pressure may be set by a caregiver for a maximum pressure ($P_{max}$), as shown by the dashed line 327. At reference line 302, when the reduced-pressure source 104 begins the on-state 320, the pressure profile 301 ($P_s$) may be about 0 mm Hg. The pressure profile 301 ($P_s$) increases to a value of about 120 mm Hg during the on-state 320. A slope of the pressure profile 301 ($P_s$) between the reference line 302 and the reference line 304 as the pressure profile 301 ($P_s$) increases from about 0 mm Hg to about 120 mm Hg may be referred to as a reduced-pressure ramp-up period 328. The reduced-pressure ramp-up period 328 corresponds to a time interval during which the pressure profile 301 ($P_s$) increases within the sealed therapeutic environment 103 from an ambient pressure ($P_{min}$) at an inflection point 303 to the maximum pressure ($P_{max}$) at an inflection point 305. The inflection point 303 is located at the intersection of the reference line 302, the dashed line 329, and pressure profile 301 ($P_s$). The inflection point 305 is located at the intersection of the pressure profile 301 ($P_s$) and the dashed line 327 between the reference line 302 and the reference line 304.

When the sealed therapeutic environment 103 reaches the therapy pressure ($P_{max}$), the reduced-pressure therapy system 101 may be programmed to maintain the therapy pressure ($P_{max}$) for a predetermined period of time. While the reduced-pressure therapy system 101 maintains the therapy pressure ($P_{max}$), the pressure profile 301 ($P_s$) may have a substantially flat slope for a reduced-pressure therapy period 330. The reduced-pressure therapy period 330 may continue until the reduced-pressure source 104 switches to the off-state 322 at the reference line 304. The reduced-pressure therapy period 330 may be a time interval of steady-state reduced pressure in the sealed therapeutic environment 103. As shown, the reduced-pressure therapy period 330 may extend from the inflection point 305 to the inflection point 307. The inflection point 307 is located at the intersection of the reference line 304, the dashed line 327, and the pressure profile 301 ($P_s$). In the reduced-pressure therapy period 330, the reduced-pressure source 104 may be operating to maintain the reduced-pressure at about the therapy pressure ($P_{max}$), for example, at about 120 mm Hg.

When the reduced-pressure source 104 switches from the on-state 320 to the off-state 322, as shown at the reference line 304 in FIG. 5, the pressure profile 301 ($P_s$) may enter a reduced-pressure ramp-down period 332, as shown in FIG. 6A. The reduced-pressure ramp-down period 332 corresponds to a time interval during which the pressure profile 301 ($P_s$) decreases within the sealed therapeutic environment 103 from the maximum pressure ($P_{max}$) to the minimum pressure ($P_{min}$). As shown in FIG. 6A, the reduced-pressure ramp-down period 332 is a portion of the pressure profile 301 ($P_s$) beginning at the inflection point 307 and ending at an inflection point 309. The inflection point 309 is located at the intersection of the pressure profile 301 ($P_s$) and the dashed line 329. As the reduced pressure profile 301 ($P_s$) decreases during the reduced-pressure ramp-down period 332, the pressure profile 301 ($P_s$) may reach the trigger pressure ($P_t$). The trigger pressure ($P_t$) represented by the dashed line 334. If the pressure profile 301 ($P_s$) reaches the trigger pressure ($P_t$), instillation of fluids may commence as shown by the reference line 306. In some embodiments, the trigger pressure ($P_t$) may be set during the manufacturing process.

When the pressure profile 301 ($P_s$) reaches about 0 mm Hg, the slope of the pressure profile 301 ($P_s$) may remain substantially flat in a soak period 336. The soak period 336 may correspond with a time interval during which there is no reduced-pressure therapy. The soak period 336 extends from the inflection point 309 to an inflection point 311. The inflection point 311 is located at the intersection of the reference line 312, the dashed line 329 and the pressure profile 301 ($P_s$). Eventually, the reduced-pressure therapy may resume at the inflection point 311 when the reduced-pressure source 104 returns to the on-state 324. Instillation of fluids, which commenced at the reference line 306 may continue to the reference line 308 as described below with respect to FIG. 7.

Continued operation of the reduced-pressure source 104 may cause the pressure profile 301 ($P_s$) illustrated in FIG. 6A to cyclically repeat. A second cycle may commence with the on-state 324 of the reduced-pressure source 104 initiating a reduced-pressure ramp-up period 341 and a reduced-pressure therapy period 343. The second cycle may have an off-state 326, initiating a reduced-pressure ramp-down period 345 and concluding at the end of a soak period 349. As further illustrated, the pressure profile 301 ($P_s$) of FIG. 6A appears to lag relative to the operation of the reduce-pressure source 104 illustrated in FIG. 5. The lag may occur due to a period of time required for the pressure in the sealed therapeutic environment 103 to respond to the operation of the reduced-pressure source 104. In other embodiments, the pressure profile 301 ($P_s$) of FIG. 6A may not lag the operation of the reduced-pressure source 104.

As described with respect to FIG. 6A and FIG. 7, the dynamic mode of the instillation therapy system 116 and the fluid source 118 may be configured to operate in coordination with the operation of the reduced-pressure therapy system 101 and the reduced-pressure source 104. In the dynamic mode, the controller 202 may know the pressure profile 301 ($P_s$) and the trigger pressure ($P_t$) as illustrated in FIG. 6A. In some embodiments, the controller 202 may determine the pressure profile 301 ($P_s$) and the trigger pressure ($P_t$) in a training mode. In some embodiments, a caregiver may provide the pressure profile 301 ($P_s$) and the trigger pressure ($P_t$) through the user interface 204.

In an illustrative embodiment, the controller 202 may monitor the pressure profile 301 ($P_s$) through the sensor 206 to provide instillation therapy. In some embodiments, the controller 202 may close the valve 208 until the pressure profile 301 ($P_s$) reaches the trigger pressure ($P_t$) following the reduced-pressure therapy period 330. When the pressure profile 301 ($P_s$) reaches the trigger pressure ($P_t$) the controller 202 may open the valve 208, as shown by reference line 306. The controller 202 may then monitor the fluid flow through the valve 208 with the flow meter 209. When the dosage has passed through the valve 208, the controller 202 may close the valve 208 as shown at the reference line 308. The dosage of fluid may remain within the sealed therapeutic environment 103 until the reduced-pressure ramp-up period 341 begins at the inflection point 309. As the on-state 324 of the reduced-pressure source 104 causes the pressure profile 301 ($P_s$) to increase, the fluid delivered during the instillation of fluids may be removed through the tube 109 to the container 112.

In some embodiments, the flow rate through the valve 208 may not be sufficient to deliver the dosage of fluid prior to the repetition of the duty cycle of the reduced-pressure source 104. In response, the controller 202 may close the valve 208 prior to the repetition of the duty cycle of the reduced-pressure source 104. For example, if the valve 208 is still open, the controller 202 may close the valve 208 at the reference line 312. If the dosage of fluid is not fully delivered based on the initial trigger pressure ($P_t$), the controller 202 may adjust the trigger pressure ($P_t$) to increase the time for fluid flow. For example, if the initial trigger pressure ($P_t$) is about 75 mm Hg reduced pressure and the controller 202 determines that the full dosage of fluid could not be delivered prior to the inflection point 311, the controller 202 may reset the trigger pressure ($P_t$) to 80 mm Hg reduced pressure as indicated by the dashed line 334a. The pressure profile 301 ($P_s$) reaches the trigger pressure ($P_t$) 334a sooner than the trigger pressure ($P_t$) 334. In response, the controller 202 may open the valve 208 sooner as indicated by the reference line 310, increasing the dosage period. In this manner, the controller 202 may adjust instillation to provide a complete dosage of fluid to the sealed therapeutic environment 103.

Figure 6B:
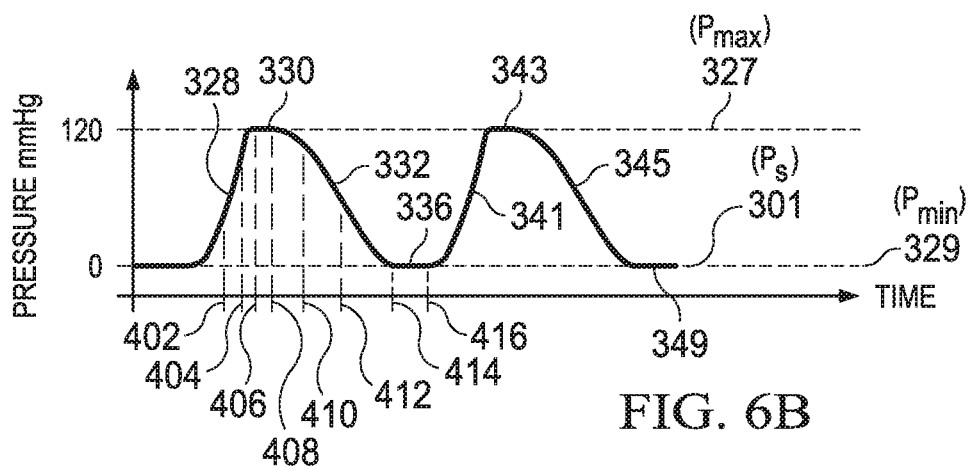
FIG. 6B is a graphical depiction of the pressure profile of FIG. 6A illustrating a training mode of the instillation therapy system of FIG. 4.

FIG. 6B is a graphical representation of the pressure profile 301 ($P_s$) of the sealed therapeutic environment 103 that may be associated with some embodiments. In FIG. 6B, the y-axis represents the absolute value of the reduced pressure measured by the sensor 206 at the fluid interface 120, and the x-axis represents time. In some embodiments, the controller 202 may operate in a training mode to determine the pressure profile 301 ($P_s$) and the duty cycle of the reduced-pressure source 104. In the training mode, the controller 202 may send a signal to the valve 208 to move the valve 208 to the closed position. The controller 202 may monitor a signal received from the sensor 206. In some embodiments, the sensor 206 may send a continuing signal that corresponds to an instantaneous pressure in the sealed therapeutic environment 103. An instantaneous pressure may refer to a pressure at the moment at which the pressure is measured. In some embodiments, the signal sent by the sensor 206 may reflect the pressure profile 301 ($P_s$) displayed graphically in FIG. 6B. The controller 202 may monitor the signal from the sensor 206 for at least one duty cycle of the reduced-pressure source 104.

The controller 202 may store the signal received from the sensor 206 at the initiation of the dynamic mode. The controller 202 may monitor the signal from the sensor 206 and compare pressures to determine the pressure profile 301 ($P_s$). For example, the controller 202 may record a reduced pressure received from the sensor 206 at a first instant in time, such as a time 402. The controller 202 may then record a reduced pressure received from the sensor 206 at a second instant in time, such as a time 404. The controller 202 may compare the reduced pressure at the time 402 and the time 404. If the reduced pressure at the time 404 is greater than the reduced pressure at the time 402, the controller 202 may store the reduced pressure at time 404 as the maximum reduced pressure ($P_{max}$). The reduced pressure at the time 404, may then be compared to a reduced pressure at a third instant in time, for example, a time 406. The process may repeat until a reduced pressure at a later instant in time is not greater than the reduced pressure at the previous instant in time. If a subsequent reduced pressure is greater than an immediately prior reduced pressure, the controller 202 may determine that the pressure profile 301 ($P_s$) is in the reduced-pressure ramp-up period 328 of FIG. 6B. In some embodiments, comparisons between pressures may occur at multiple instances between each time shown.

If the reduced pressure at the second instant in time is about the same as the reduced pressure at the first instant in time, such as at the time 406 and a time 408, the controller 202 may determine that the pressure profile 301 ($P_s$) is in the reduced-pressure therapy period 330 or the soak period 336. The reduced pressure at the time 406 and the time 408 may then be compared to the maximum reduced pressure ($P_{max}$), and if the reduced pressure at the time 406 and the time 408 is about the same as the maximum reduced pressure ($P_{max}$), the controller 202 may determine that the reduced pressure profile 301 ($P_s$) is in the reduced-pressure therapy period 330.

If the reduced pressure at the second instant in time is less than the reduced pressure at the first instant in time, such as at the time 408 and a time 410, the controller 202 may store the reduced pressure at the time 410 as the minimum reduced pressure ($P_{min}$). The reduced pressure at the time 410 may then be compared to a reduced pressure at a third instant in time, repeating the process until a reduced pressure at a later instant in time is not less than the reduced pressure at the previous instant in time. If a subsequent reduced pressure is less than an immediately prior reduced pressure, such as at the time 410 and a time 412, the controller 202 may determine that the pressure profile 301 ($P_s$) is in the reduced-pressure ramp-down period 332 of FIG. 6B.

If the reduced pressure at the second instant in time is about the same as the reduced pressure at the first instant in time, such as at a time 414 and a time 416, the controller 202 may determine that the pressure profile 301 ($P_s$) is in the reduced-pressure therapy period 330 or the soak period 336. The reduced pressure at the time 414 and the time 416 may then be compared to the minimum reduced pressure ($P_{min}$), and if the reduced pressure at the time 414 and the time 416 is about the same as the minimum reduced pressure ($P_{min}$), the controller 202 may determine that the pressure profile 301 ($P_s$) is in the soak period 336 of FIG. 6B.

The controller 202 may continue to monitor the signal from the sensor 206, following the process previously described. If the controller 202 determines that the pressure profile 301 ($P_s$) is repeating, for example, the controller 202 repeatedly identifies the same maximum reduced pressure ($P_{max}$) and minimum reduced pressure ($P_{min}$) at about the same time intervals, the controller 202 may exit the training mode.

During the time in which the controller 202 monitors the signal from the sensor 206, the controller 202 may store the pressure profile 301 ($P_s$) in a memory of the controller 202. The controller 202 may also store time intervals between the maximum reduced pressure ($P_{max}$) and minimum reduced pressure ($P_{min}$) to determine the on-state 320, the on-state 324, the off state 322, and the off-state 326 of the reduced-pressure source 104. The controller 202 may then determine one or more parameters of the reduced-pressure therapy as described above. In some embodiments, the parameters may include the maximum pressure ($P_{max}$) in the sealed therapeutic environment 103 and the minimum pressure ($P_{min}$) in the sealed therapeutic environment 103. In some embodiments, the controller 202 may calculate an expected trigger pressure ($P_t$) based on the measured time intervals between the on-states 320/324 of the reduced-pressure source 104 and an expected flow rate through the valve 208. In some embodiments, the controller 202 may provide a signal to the user interface 204 so that the parameters may be displayed on the user interface 204. In some embodiments, the external environment may interact with the user interface 204 to override and replace the parameters determined from the training mode.

In some embodiments, the controller 202 may store an expected reduced-pressure ramp-down period 332. For example, the controller 202 may determine an expected slope of the pressure profile 301 ($P_s$) during the reduced-pressure ramp-down period 332 when fluid is being supplied to the sealed therapeutic environment 103. The controller 202 may monitor the signal from the sensor 206 during the reduced-pressure ramp-down period 332. During instillation therapy, the actual reduced-pressure ramp-down period 332 may deviate from the expected reduced-pressure ramp-down period 332 while providing a dosage of fluid. A deviation of the reduced-pressure ramp-down period 332 may indicate that the fluid flow through the fluid interface 120 consists of an unexpected fluid, for example a gas rather than an instillation fluid. If a gas is flowing through the fluid interface 120, the fluid reservoir 210 may be empty. If the actual reduced-pressure ramp-down period 332 deviates from the expected reduced-pressure ramp-down period 332, the controller 202 may signal the user interface 204 to display an alarm indicating that the fluid reservoir 210 may be empty.

Figure 9:
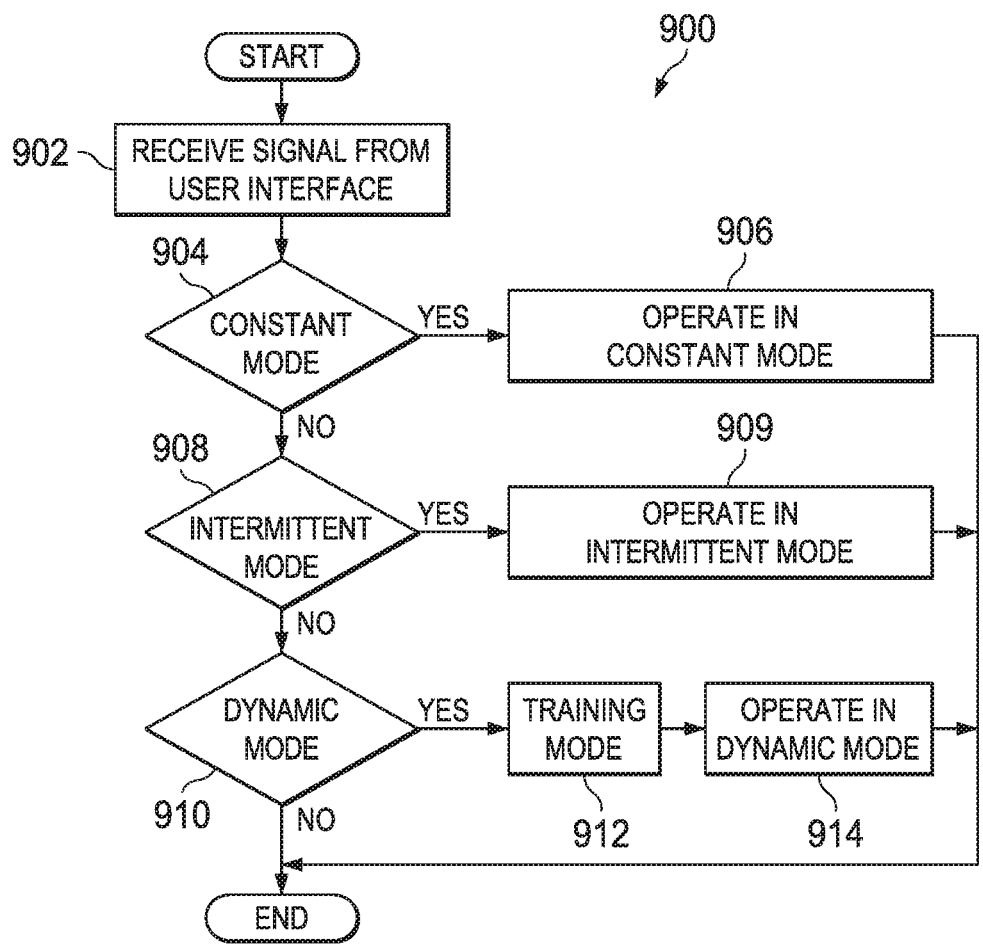
FIG. 9 is a block diagram illustrating operative steps of the fluid source of FIG. 4.

FIG. 9 illustrates a flow chart 900 that depicts logical operational steps performed by, for example, the instillation therapy system 116 of FIG. 1, which may be implemented in accordance with an embodiment. The system receives a signal from a user interface at block 902. For example, the controller 202 may receive a signal from the user interface 204. Next, at block 904, the system may determine whether the signal represents a selection of a constant mode. Illustratively, the controller 202 may determine if the signal represents a selection of the constant mode. If the system determines that the signal represents a selection of the constant mode at block 904 (YES), the system operates in the constant mode to deliver fluids for a predetermined period of time at block 906. For example, the controller 202 may open the valve 208, permitting fluid flow from the fluid reservoir 210 to the sealed therapeutic environment 103.

If the system determines that the signal does not represent a selection of the constant mode at block 904 (NO), the system determines if the signal represents a selection of the intermittent mode. For example, the controller 202 determines if the signal represents a selection of the intermittent mode. If the system determines that the signal represents a selection of the intermittent mode at block 908 (YES), the system operates in the intermittent mode such that a predetermined number of dosages may be delivered to the sealed therapeutic environment 103 over a predetermined period of time at block 909. If the system determines that the signal does not represent a selection of the intermittent mode at block 908 (NO), the system determines if the signal represents a selection of the dynamic mode at block 910. If the system determines the signal represents a selection of the dynamic mode at block 910 (YES), the system operates in the training mode at block 912 after which the system operates in the dynamic mode to deliver fluids at block 914 for a predetermined period of time. For example, the controller 202 may operate in the training mode and then the controller 202 may deliver fluids in accordance with the pressure profile 301 ($P_s$) determined in the training mode of block 912.

Figure 10:
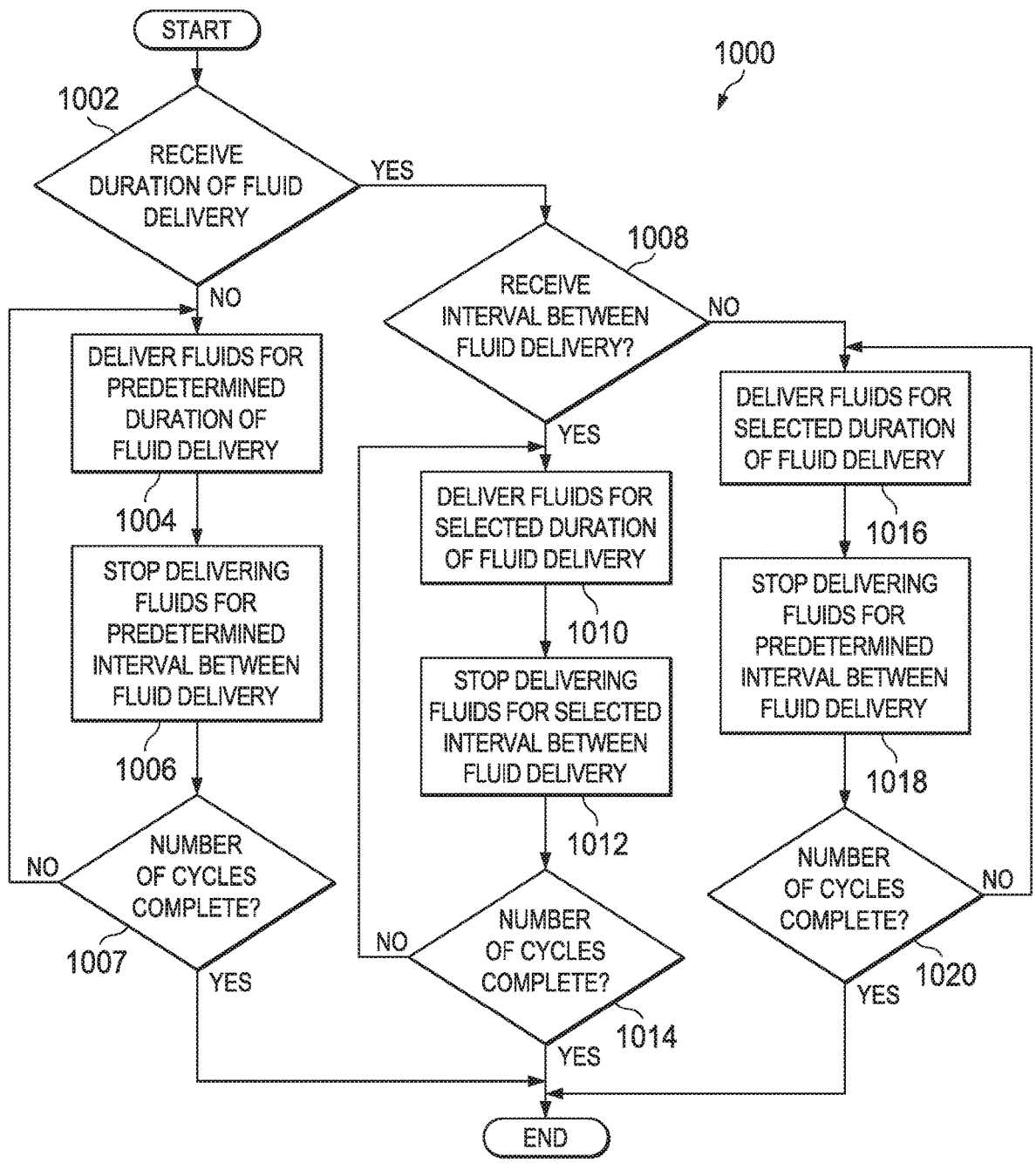
FIG. 10 is a block diagram illustrating operative steps of an intermittent mode of operation of the fluid source of FIG. 4.

FIG. 10 illustrates a flow chart 1000 that depicts logical operational steps performed by, for example, the instillation therapy system 116 of FIG. 1 during the intermittent mode, which may be implemented in accordance with an embodiment. In an illustrative embodiment, the system determines if the system received a selection of a duration of fluid delivery at block 1002. For example, the controller 202 may determine if the user interface 204 received a selection of a duration of fluid delivery. If the system determines that no duration of fluid delivery was selected at block 1002, the system delivers fluids for a pre-determined duration of fluid delivery at block 1004. For example, the controller 202 may open the valve 208 for a predetermined duration of fluid delivery, such as one minute. The system stops delivering fluids for a predetermined interval between fluid delivery at block 1006. For example, the controller 202 may close the valve 208 for a predetermined interval between fluid delivery, such as 1 minute. The system then determines whether a predetermined number of on-off cycles has occurred at block 1007. If a predetermined number of on-off cycles has not occurred at block 1007 (NO), the system repeats beginning at block 1004. If a predetermined number of on-off cycles has occurred at block 1007 (YES), the intermittent mode ends.

If the system determines that a duration of fluid delivery was selected at block 1002 (YES), the system determines if an interval between fluid delivery was selected at block 1008. If the system determines that an interval between fluid delivery was selected at block 1008 (YES), the system delivers fluids for the selected duration of fluid delivery at block 1010 and stops delivering fluids for the interval between fluid delivery at block 1012. For example, the controller 202 may open the valve 208 for a selected duration of fluid delivery received through the user interface 204, such as two minutes and the controller 202 may close the valve 208 for a selected interval between fluid delivery, such as three minutes. The system then determines whether a predetermined number of on-off cycles has occurred at block 1014. If a predetermined number of on-off cycles has not occurred at block 1014 (NO), the system repeats beginning at block 1010. If a predetermined number of on-off cycles has occurred at block 1014 (YES), the intermittent mode ends.

If the system determines that no interval between fluid delivery was selected at block 1008 (NO), the system delivers fluids for the selected duration of fluid delivery at block 1016 and stops delivering fluids for a predetermined interval between fluid delivery at block 1018. For example, the controller 202 may open the valve 208 for a selected duration of fluid delivery received through the user interface 204, such as two minutes, and the controller 202 may close the valve 208 for a predetermined interval between fluid delivery, such as two minutes. The system then determines whether a predetermined number of on-off cycles has occurred at block 1020. If a predetermined number of on-off cycles has not occurred at block 1020 (NO), the system repeats beginning at block 1016. If a predetermined number of on-off cycles has occurred at block 1020 (YES), the intermittent mode ends.

Figure 11:
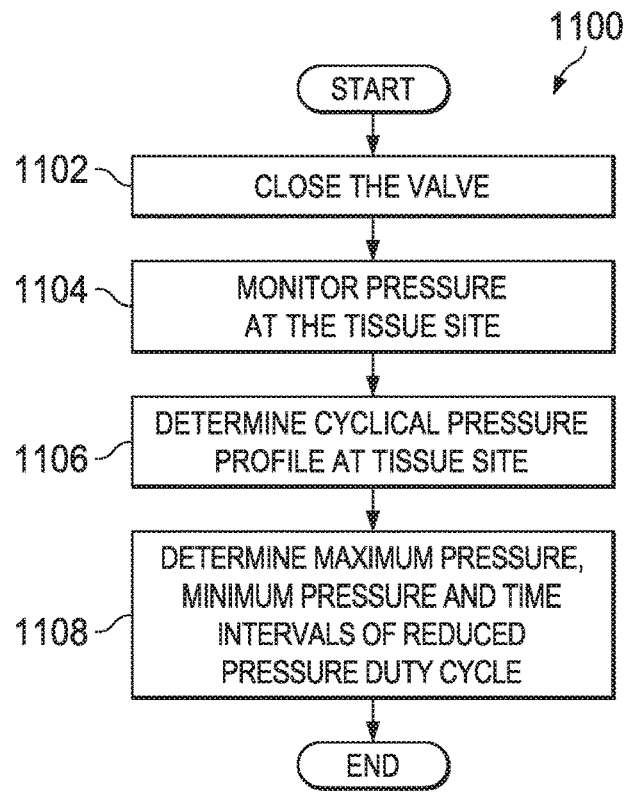
FIG. 11 is a block diagram illustrating operative steps of a training mode of operation of the fluid source of FIG. 4.

FIG. 11 illustrates a flow chart 1100 that depicts logical operational steps performed by, for example, the instillation therapy system 116 of FIG. 1 during the training mode, which may be implemented in accordance with an embodiment. The system closes a valve at block 1102. For example, the controller 202 may close the valve 208. The system monitors the pressure at the tissue site at block 1104. For example, the controller 202 monitors the signal representing the pressure from the sensor 206. The system determines a cyclical pressure profile at the tissue site at block 1106. For example, the controller 202 may determine the pressure profile 301. The system may determine a maximum pressure, a minimum pressure, and the time intervals for the on period and the off period of the duty cycle of the reduced-pressure source at block 1108. For example, the controller 202 may determine a maximum pressure ($P_{max}$), a minimum pressure ($P_{min}$), and the time interval of the on-states 320/324 and the off-states 322/326 of the reduced-pressure source 104.

Figure 12:
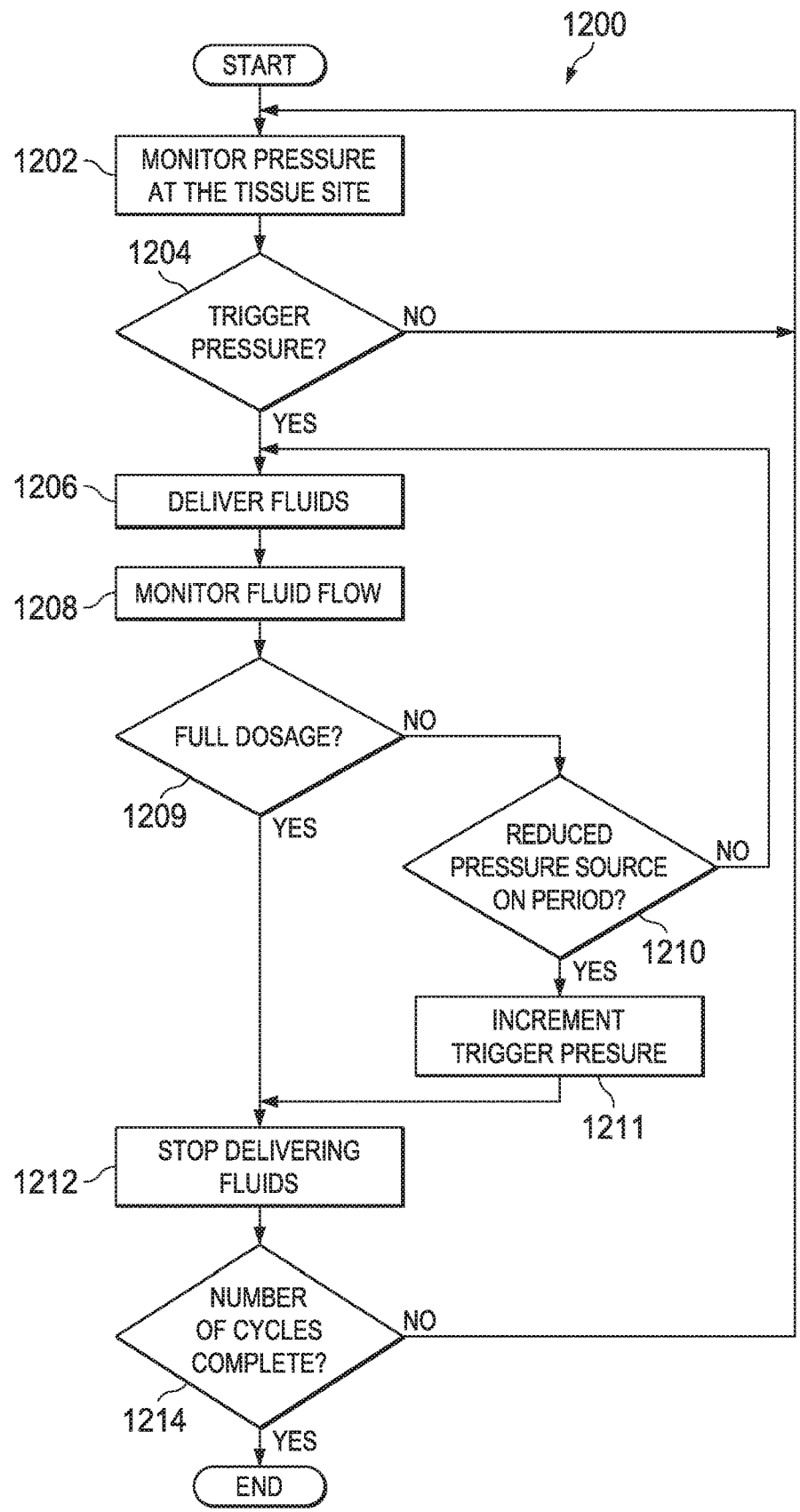
FIG. 12 is a block diagram illustrating operative steps of a dynamic mode of operation of the fluid source of FIG. 4.

FIG. 12 illustrates a flow chart 1200 that depicts logical operational steps performed by, for example, the instillation therapy system 116 of FIG. 1 during fluid delivery in the dynamic mode, which may be implemented in accordance with an embodiment. The system monitors the pressure at the tissue site at block 1202. For example, the controller 202 monitors the signal from the sensor 206 representing the pressure in the sealed therapeutic environment 103. The system determines if the trigger pressure has been reached at block 1204. For example, the controller 202 may determine if the trigger pressure 334 ($P_t$) has been reached by the pressure profile 301 ($P_s$). If the system determines that the trigger pressure has not been reached at block 1204 (NO), the system continues to monitor the pressure at the tissue site.

If the system determines that the trigger pressure has been reached at block 1204 (YES), the system delivers fluids at block 1206. For example, the controller 202 opens the valve 208 to permit fluid flow to the sealed therapeutic environment 103. The system monitors fluid flow at block 1208. For example, the controller 202 monitors the signal from the flow meter 209 representing the fluid flow through the valve 208. The system determines if a full fluid dosage has been delivered at block 1209. For example, the controller 202 determines if the full dosage of fluid has passed through the valve 208.

If the system determines that the full fluid dosage has not been delivered at block 1209 (NO), the system determines whether the reduced-pressure source is entering an on period at block 1210. For example, the controller 202 may monitor how long the reduced-pressure source 104 has been in the off-state 322 to determine if the reduced-pressure source 104 is about to enter the on-state 324. If the system determines that the reduced-pressure source is not entering an on-state at block 1210 (NO), the system continues delivering fluids at block 1206. If the system determines that the reduced-pressure source is entering an on-state at block 1210 (YES), the system increments the trigger pressure at block 1211, and the system stops delivering fluids at block 1212. For example, the controller 202 may adjust the trigger pressure to begin fluid delivery at a higher reduced pressure and close the valve 208.

If the system determines that the full dosage of fluid has been delivered at block 1209 (YES), the system stops delivering fluids at block 1212. For example, the controller 202 may close the valve 208, stopping fluid delivery. The system determines whether a predetermined number of on-off cycles of fluid delivery has been completed at block 1214. If the system determines that a predetermined number of on-off cycles of fluid delivery has been completed at block 1214 (YES), the process ends. If the system determines that a predetermined number of on-off cycles of fluid delivery has not been completed at block 1214 (NO), the system repeats beginning at block 1202.

Figure 13:
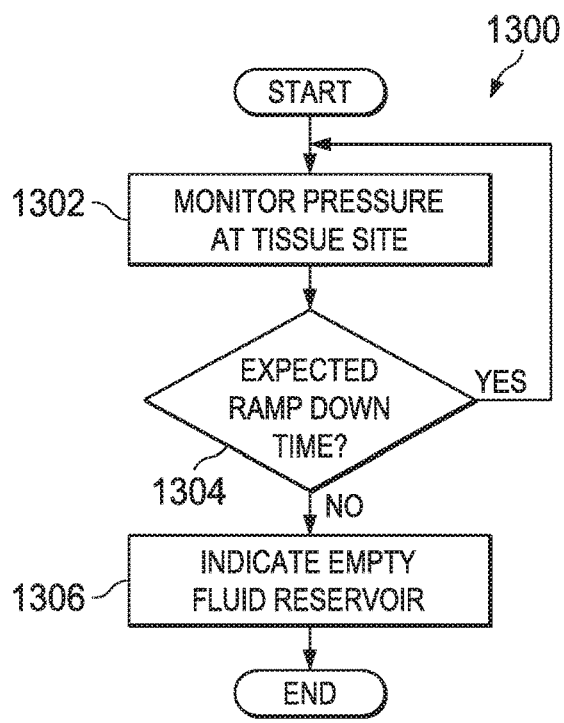
FIG. 13 is a block diagram illustrating additional operative steps of the dynamic mode of operation of the fluid source of FIG. 4.

FIG. 13 illustrates a flow chart 1300 that depicts logical operational steps performed by, for example, the instillation therapy system 116 of FIG. 1 during fluid delivery, which may be implemented in accordance with an embodiment. In the illustrated flow chart, the instillation therapy system 116 may determine if the fluid reservoir 210 is empty. The system monitors the pressure at the tissue site at block 1302. For example, the controller 202 monitors the signal from the sensor 206 representing the pressure in the sealed therapeutic environment 103. The system determines if a reduced-pressure ramp-down period is the expected reduced-pressure ramp-down period at block 1304. For example, the controller 202 may determine if a reduced-pressure ramp-down period is the expected reduced-pressure ramp-down period 332. If the system determines that the reduced-pressure ramp-down period is the expected reduced-pressure ramp-down period at block 1304 (YES), the system repeats at block 1302. If the system determines that the reduced-pressure ramp-down period is not the expected reduced-pressure ramp-down period 332, the system indicates an empty fluid reservoir at block 1306 and ends. For example, the controller 202 may activate an alarm on the user interface 204 indicating an empty fluid reservoir 210.

The systems and methods described herein may provide significant advantages, some of which have already been mentioned. For example, the instillation therapy system may provide a combined reduced-pressure therapy and instillation therapy system that may be simple to set-up. The instillation therapy system may also provide an instillation system that may be used with an independent reduced-pressure system that may be capable of intermittent therapy. The instillation therapy system may also use the reduced-pressure source as the mechanism to draw the fluid to the sealed therapeutic environment, allowing the instillation therapy system to use simpler components. The instillation therapy system may also overcome a head pressure differential. The instillation therapy system may provide feedback on critical parameters related to the performance of a reduced-pressure source regarding the level of reduced-pressure delivered to a sealed therapeutic environment. The instillation therapy system may be configured manually, or through a training mode. The instillation therapy system can also deliver fluid in sync with an intermittent reduced-pressure cycle or in a continuous manner or variations in between.

It should be apparent from the foregoing that an invention having significant advantages has been provided. While shown in only a few forms, the systems and methods illustrated are susceptible to various changes and modifications without departing from the spirit thereof.

We claim:

1. A system for providing instillation therapy to a tissue site, the system comprising:
   a fluid interface configured to be fluidly coupled to the tissue site;
   a pressure sensor fluidly coupled to the fluid interface and configured to measure a pressure proximate the tissue site;
   a valve fluidly coupled to the fluid interface and having an open position configured to permit fluid communication through the valve and a closed position configured to prevent fluid communication through the valve;
   a flow meter configured to be fluidly coupled between the valve and the fluid interface and monitor a fluid flow rate through the valve to determine a volume of fluid flow;
   a fluid reservoir fluidly coupled to the valve; and
   a controller communicatively coupled to the pressure sensor and the valve, the controller configured to monitor the pressure measured by the pressure sensor and a volume of fluid flow through the flow meter and, in response, operate the valve;
   the controller being further configured to open the valve in response to the pressure sensor detecting a predetermined pressure and to close the valve in response to the flow meter determining a predetermined volume of fluid has been delivered to the tissue site.

2. The system of claim 1, wherein the controller is configured to operate the valve in response to one or more of a maximum reduced pressure, a minimum reduced pressure, a trigger pressure, an on-state and an off-state of a reduced-pressure therapy system, and a duration of fluid delivery and an interval of fluid delivery.

3. The system of claim 1, wherein the controller is configured to determine a pressure profile in response to the pressure measured by the pressure sensor.

4. The system of claim 3, wherein the controller is configured to determine one or more operating parameters in response to the pressure profile.

5. The system of claim 4, wherein the one or more operating parameters comprise one or more of a maximum reduced pressure, a minimum reduced pressure, a trigger pressure, and an on-state and an off-state of a reduced-pressure therapy system.

6. The system of claim 1, further comprising a user interface operationally coupled to the controller and configured to present one or more operating parameters of the system.

7. The system of claim 6, wherein the one or more operating parameters comprise one or more of a maximum reduced pressure, a minimum reduced pressure, a trigger pressure, and an on-state and an off-state of a reduced-pressure therapy system.

8. The system of claim 6, wherein the user interface is further configured to receive operational input and communicate the operational input to the controller.

9. The system of claim 8, wherein the operational input may comprise one or more of a maximum reduced pressure, a minimum reduced pressure, a trigger pressure, a duration of fluid delivery, and an interval of fluid delivery.

10. The system of claim 1, further comprising a pump fluidly coupled between the fluid reservoir and the valve, the pump being operationally coupled to the controller.

11. The system of claim 1, further comprising a disposable connector fluidly coupled between the pressure sensor and the fluid interface.

12. The system of claim 1, further comprising at least one sensor fluidly coupled to a tube fluidly coupling the valve to the fluid interface and further operationally coupled to the controller, the at least one sensor configured to detect blockages in the tube.

13. The system of claim 1, further comprising:
   a reduced-pressure interface configured to be fluidly coupled to the tissue site;
   a reduced-pressure pressure source configured to be fluidly coupled to the reduced-pressure interface; and
   a fluid container configured to be fluidly coupled between the reduced-pressure interface and the reduced-pressure source.

* * * * *